(12) United States Patent
Yan et al.

(10) Patent No.: US 12,357,251 B2
(45) Date of Patent: Jul. 15, 2025

(54) IMAGE ACQUISITION METHOD, IMAGING SYSTEM, CALIBRATION EQUIPMENT AND STORAGE MEDIUM

(71) Applicant: OUR UNITED CORPORATION, Xi'an (CN)

(72) Inventors: Hao Yan, Xi'an (CN); Dalin Liu, Xi'an (CN); Shaojie Chang, Xi'an (CN)

(73) Assignee: OUR UNITED CORPORATION, Xi'an (CN)

( * ) Notice: Subject to any disclaimer, the term of this patent is extended or adjusted under 35 U.S.C. 154(b) by 245 days.

(21) Appl. No.: 18/175,916

(22) Filed: Feb. 28, 2023

(65) Prior Publication Data
US 2023/0240634 A1  Aug. 3, 2023

(30) Foreign Application Priority Data
Dec. 31, 2021  (CN) .......................... 202111665443.9

(51) Int. Cl.
*A61B 6/00*  (2024.01)
*A61B 6/40*  (2024.01)
*A61B 6/58*  (2024.01)

(52) U.S. Cl.
CPC ............ *A61B 6/483* (2013.01); *A61B 6/4085* (2013.01); *A61B 6/584* (2013.01)

(58) Field of Classification Search
None
See application file for complete search history.

(56) References Cited

U.S. PATENT DOCUMENTS

| | | | |
|---|---|---|---|
| 11,602,315 B2 * | 3/2023 | Zhao | .......................... A61B 6/03 |
| 2012/0207370 A1 | 8/2012 | Fahimian | |
| 2013/0004042 A1 | 1/2013 | Yang | |
| 2018/0325485 A1 | 11/2018 | Maslowski | |
| 2022/0309632 A1 * | 9/2022 | Li | .......................... H04N 25/61 |
| 2023/0011644 A1 * | 1/2023 | Zhao | ..................... A61B 6/5282 |
| 2024/0346693 A1 * | 10/2024 | Namgung | ............... G01B 11/25 |

FOREIGN PATENT DOCUMENTS

| | | |
|---|---|---|
| CN | 101158653 A | 4/2008 |
| CN | 101566590 A | 10/2009 |
| CN | 101987021 A | 3/2011 |
| CN | 102068270 A | 5/2011 |
| CN | 113164138 A | 7/2021 |
| CN | 214761130 U | 11/2021 |
| KR | 20180107899 A | 10/2018 |

* cited by examiner

*Primary Examiner* — Hoon K Song
(74) *Attorney, Agent, or Firm* — Kolitch Romano Dascenzo Gates LLC

(57) ABSTRACT

Provided are an image acquisition method, an imaging system, calibration equipment and a storage medium. The image acquisition method includes: acquiring a projection image formed by an imaging beam passing through a barrier array plate; acquiring scattered sampling points corresponding to the barrier posts in the projection image; interpolating a vacancy between every adjacent scattered sampling points to obtain interpolated sampling points; and acquiring a scattering distribution map corresponding to the projection image based on the scattered signals of the scattered sampling points and of the interpolated sampling points.

20 Claims, 8 Drawing Sheets

IMAGE ACQUISITION METHOD, IMAGING SYSTEM, CALIBRATION EQUIPMENT AND STORAGE MEDIUM

CROSS-REFERENCE TO RELATED APPLICATIONS

This application claims the priority to the Chinese Patent Application No. with the application number 202111665443.9 and entitled "SCATTERING ESTIMATION METHOD, IMAGING SYSTEM, CORRECTION DEVICE, AND STORAGE MEDIUM" filed on Dec. 31, 2021, the entire contents of which are incorporated herein by reference.

TECHNICAL FIELD

The present disclosure relates to an image acquisition method, an imaging system, calibration equipment and a storage medium.

BACKGROUND OF THE INVENTION

Computed tomography (CT) technology in clinical medicine is one of the important symbols of medical technology progress in the 20th century. With the development of science and technology, great changes have taken place in CT scanning methods, and cone beam CT (CBCT) has also entered the practical stage.

Cone-beam CT is cone-beam projection computed tomography imaging equipment. Its principle is that an imaging source (such as an X-ray tube) performs circular digital projection around an object to be detected with a low dose of radiation. After data obtained after multiple digital projections around the object to be detected is reconstructed, a three-dimensional reconstructed image of the object to be detected can be obtained. The scattering of X-ray photons during the cone beam CT imaging process affects the quality of the reconstructed image. For example, it causes a decrease in the contrast of the 3D reconstructed image, and then the CT value of the object to be detected based on the 3D reconstructed image is inaccurate.

At present, a more accurate three-dimensional reconstruction image of the object to be detected is obtained by determining the scattering of photons. However, the accuracy of determining the scattering of photons in the cone-beam CT imaging process needs to be improved.

SUMMARY OF THE INVENTION

The present disclosure provides an image acquisition method, an imaging system, calibration equipment, and a storage medium.

According to some embodiments, the present disclosure provides an image acquisition method. The image acquisition method includes:
  acquiring a projection image formed by an imaging beam passing through a barrier array plate, wherein the barrier array plate includes a plurality of barrier posts;
  acquiring scattered sampling points corresponding to the barrier posts in the projection image, wherein the scattered sampling points are disposed in shaded areas that are occluded by the barrier posts in the projection image;
  interpolating a vacancy between every adjacent scattered sampling points based on scattered signals of the scattered sampling points to obtain interpolated sampling points, a scattered signal of any point in the projection image referring to a scattered ray signal in a ray signal forming the point, and the vacancy referring to an area between shaded areas where every adjacent scattered sampling points are located; and
  acquiring a scattering distribution map corresponding to the projection image based on the scattered signals of the scattered sampling points and of the interpolated sampling points, wherein the scattering distribution map is configured to characterize scattering of the imaging beam.

According to some embodiments, the present disclosure provides an imaging system. The imaging system includes:
  a gantry;
  an imaging source disposed on the gantry;
  an imager disposed on the gantry opposite to the imaging source;
  a barrier array plate gantry between the imaging source and the imager, wherein the barrier array plate includes a plurality of barrier posts;
  calibration equipment connected to the imager, wherein the calibration equipment is configured to:
  acquire a projection image formed by an imaging beam passing through the barrier array plate; acquire scattered sampling points corresponding to the barrier posts in the projection image, wherein the scattered sampling points are disposed in shaded areas that are occluded by the barrier posts in the projection image; interpolate a vacancy between every adjacent scattered sampling points based on scattered signals of the scattered sampling points to obtain interpolated sampling points, a scattered signal of any point in the projection image referring to a scattered ray signal in a ray signal forming the point, and the vacancy referring to an area between shaded areas where every adjacent scattered sampling points are located; and acquire a scattering distribution map corresponding to the projection image based on the scattered signals of the scattered sampling points and of the interpolated sampling points, wherein the scattering distribution map is configured to characterize scattering of the imaging beam.

According to some embodiments, the present disclosure provides calibration equipment. The calibration equipment includes a processor and a memory storing a computer program executable by the processor, wherein the processor, when loading and executing the computer program, is caused to perform the image acquisition method described in any of the above embodiments.

According to some embodiments, the present disclosure provides a non-transitory storage medium storing a computer program therein, wherein the computer program, when loaded and executed by a processor, causes the processor to perform the image acquisition method described in any of the above embodiments.

According to some embodiments, the present disclosure provides a computer program product including instructions. The computer program product when run by a computer, causes the computer to perform the image acquisition method described in any of the embodiments.

According to some embodiments, the present disclosure provides a chip including at least one of a programmable logic circuit or a program instruction. The chip, when running, implements the image acquisition method described in any of the above embodiments.

Figure 1:
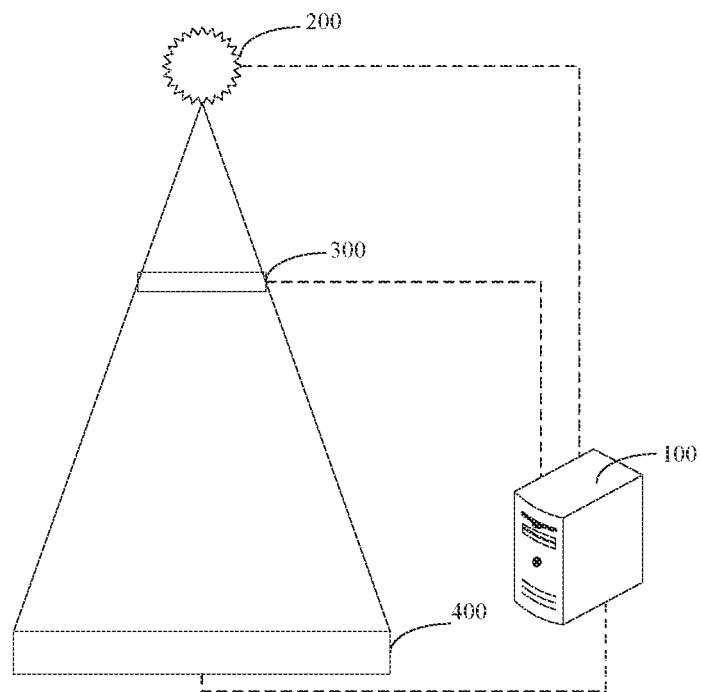
FIG. 1 is a schematic structural diagram of an imaging system according to some embodiment of the present disclosure.

Reference signs: 100—calibration equipment; 20—memory; 30—processor; 40—communication unit; 200—imaging source; 300—barrier array plate; 400—imager.

DETAILED DESCRIPTION

The technical solutions in the embodiments of the present disclosure are described clearly and completely hereinafter in conjunction with the accompanying drawings in the embodiment of the present disclosure. Apparently, the described embodiments are merely some of the embodiments of the present disclosure, not all of them. Based on the embodiments in the present disclosure, all other embodiments obtained by those skilled in the art without making creative efforts belong to the scope of protection of the present disclosure.

In the description of the present disclosure, it should be understood that orientations or positional relationships indicated by terms "center", "up", "down", "left", "right", "vertical", "horizontal", or "inner", etc. are based on orientations or positional relationships shown in the drawings, and are merely for the convenience of describing the present disclosure and simplifying the description, rather than indicating or implying that the referred device or element must have a specific orientation, or must be constructed and operated in a specific orientation, and therefore, it shall not be construed as limiting the present disclosure. In addition, terms "first" and "second" are used for descriptive purposes only, and shall not be interpreted as indicating or implying relative importance or implicitly specifying the quantity of indicated technical features. Thus, a feature defined by "first" or "second" may explicitly or implicitly include one or more features. In the description of the present disclosure, "plurality" means two or more, unless otherwise specifically defined.

In the description of the present disclosure, it should be noted that unless otherwise specified and limited, the term "connected" should be understood in a broad sense. By way of example, it may be a fixed connection, a detachable connection, or an integral connection; it may be a mechanical connection, an electrical connection, or mutual communication; it may be a direct connection, or an indirect connection through an intermediate medium, or communication between two components or an interaction relationship between two components. Those of ordinary skill in the art can understand the specific meanings of the above terms in the present disclosure according to specific situations.

In the present disclosure, unless otherwise expressly specified and limited, a first feature being (or arranged) "above" or "below" a second feature may include direct contact or indirect contact via another feature between the first and second features.

The disclosure below provides many different implementations or examples for realizing different structures of the present disclosure. To simplify the disclosure of the present disclosure, components and arrangements of specific examples are described below. Of course, they are examples only and are not intended to limit the present disclosure. Furthermore, in the present disclosure, reference numerals and/or reference letters may be repeated in various instances for simplicity and clarity, which does not in itself indicate a relationship between the various embodiments and/or arrangements discussed.

As mentioned in the background section, the accuracy of determining the scattering of photons during cone-beam CT imaging still needs to be improved.

Some embodiments of the present disclosure provide an image acquisition method, an imaging system, calibration equipment and a storage medium, which can effectively determine the distribution of scattered signals in a projection image, and improve the determination accuracy of the scattering of an imaging beam forming the projection image, and a more accurate image of an object to be detected can be obtained based on the scattering.

With reference to FIG. 1, FIG. 1 is a schematic structural diagram of an imaging system according to some embodiments of the present disclosure. As shown in FIG. 1, the imaging system includes an imaging source 200, a barrier array plate 300, an imager 400, calibration equipment 100 and a gantry (not shown in the figure). The gantry is the main structure of the imaging system and is configured to support other components. In this embodiment, the imaging source 200 and the imager 400 are arranged on the gantry opposite to each other.

In the embodiments, the imaging source 200 is (but is not limited to) a ray source such as an X-ray source or a γ-ray source. The imaging source 200 generates an imaging beam (i.e., a ray beam) to scan an object to be detected. The object to be detected is a human body, a phantom, or an animal, as long as it is an object that can be imaged by the imaging system.

In the embodiments, the imager 400 is a detector configured to receive rays emitted by the imaging source 200, convert the received rays into visible light, convert the visible light into an electrical signal via photoelectric conversion, and then convert the electrical signal into a digital signal via an analog/digital converter to obtain projection image data.

Figure 2:
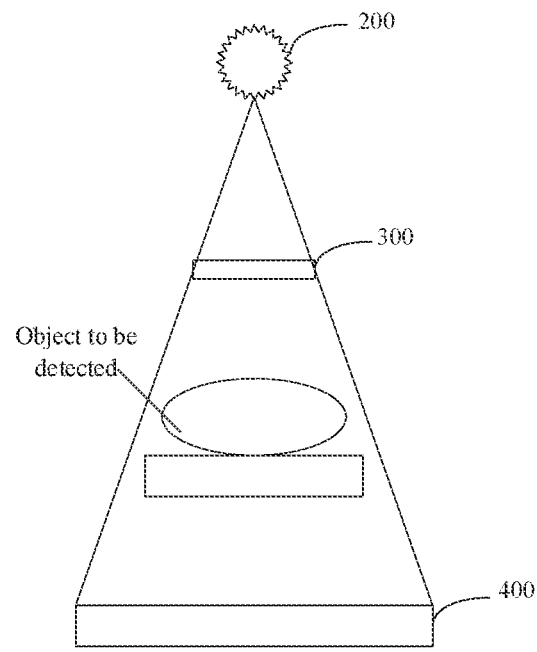
FIG. 2 is a schematic diagram of an application scenario of the imaging system according to some embodiments of the present disclosure.

The rays (also referred to as ray signals) received by the imager 400 are rays passing through the object to be detected, and the obtained projection image data is projection image data of the object to be detected. After that, an image of the object to be detected is reconstructed based on the projection image data of the object to be detected. However, when the imaging source 200 scans the object to be detected, the rays scatter on the object to be detected, which adversely affects the quality of the reconstructed image. In order to reduce the impact of scattering on the quality of the reconstructed image, the barrier array plate 300 is arranged between the imager 400 and the imaging source 200. FIG. 2 is a schematic diagram of an application scenario of the imaging system according to some embodiments of the present disclosure. As shown in FIG. 2, the barrier array plate 300 is arranged between the imaging source 200 and the object to be detected. The barrier array plate 300 is also arranged between the object to be detected and the imager 400, and the position of the barrier array plate 300 may be set according to actual needs.

In the embodiments, the barrier array plate 300 is parallel to an irradiation surface of the imaging source 200, and a plurality of barrier posts are arranged on the barrier array plate 300. The positions of the barrier posts may be set arbitrarily, that is, the arrangement positions of the barrier posts are not limited, as long as a vacancy exists between the barrier posts. The barrier array plate in the present disclosure is also referred to as a beam stop array (BSA).

In the embodiments, the barrier posts are made of high-attenuation material such as lead or tungsten. By arranging the barrier array plate between the imaging source 200 and the imager 400, during the imaging process, the rays emitted from the imaging source 200 are occluded by the barrier posts in the barrier array plate, such that shaded areas corresponding to the barrier posts are formed on the imager 400. By way of example, if 20 barrier posts are provided on the barrier array plate 300, 20 shaded areas (shaded points) will be formed on the imager 400.

Since ray signals emitted from the imaging source 200 that are transmitted linearly cannot be received in the shaded areas but the ray signals scatter during transmission in the imaging system and scattered ray signals are transmitted to the shaded areas, the ray signals received in the shaded areas include the scattered ray signals (referred to as scattered signals). In the embodiments, the ray signals received in the shaded areas are considered as scattered signals. According to the low-frequency characteristics of the scattered signals and the scattered signals in the shaded areas, the scattered signals are interpolated to determine the distribution of the overall scattered signals in the projection image, which represents the scattering of the rays (i.e., the above imaging beam) forming the projection image.

In the embodiments, any point in the projection image is formed by ray signals transmitted to the point (also referred to as ray signals of the point or signals of the point), and any area in the projection image is formed by ray signals transmitted to the area (also referred to as ray signals of the area or signals of the area). The ray signals of the points in the shaded areas that are occluded by the barrier posts in the projection image include scattered ray signals, excluding ray signals emitted by the imaging source that are transmitted linearly. The ray signals of the points in the areas that are not occluded by the barrier posts in the projection image include scattered ray signals and unscattered ray signals (such as ray signals emitted by the imaging source that are transmitted linearly). The scattered ray signals in the ray signals of any point in the projection image are referred to as the scattered signals of the point, and the scattered ray signals in the ray signals of any area in the projection image are referred to as the scattered signals of the area.

In order to determine the distribution of the overall scattered signals in the projection image, in the embodiments, the calibration equipment 100 is connected to the imager 400. The calibration equipment 100 is configured to acquire a projection image formed by an imaging beam passing through the barrier array plate 300 and scattered sampling points corresponding to the barrier posts in the barrier array plate 300 in the projection image, where the scattered sampling points corresponding to the barrier posts are disposed in shaded areas corresponding to the barrier posts; interpolate a vacancy between every adjacent scattered sampling points based on scattered signals of the scattered sampling points to obtain interpolated sampling points, a scattered signal of each scattered sampling point referring to a scattered ray signal in a ray signal forming the scattered sampling point, and the vacancy between the scattered sampling points referring to an area between shaded areas where the scattered sampling points are located; and acquire a scattering distribution map corresponding to the projection image based on the scattered signals of the scattered sampling points and of the interpolated sampling points, the scattered signals of the interpolated sampling points referring to scattered ray signals in the ray signals forming the interpolated scattered points, where the scattering distribution map is configured to characterize scattering of the imaging beam.

Figure 3:
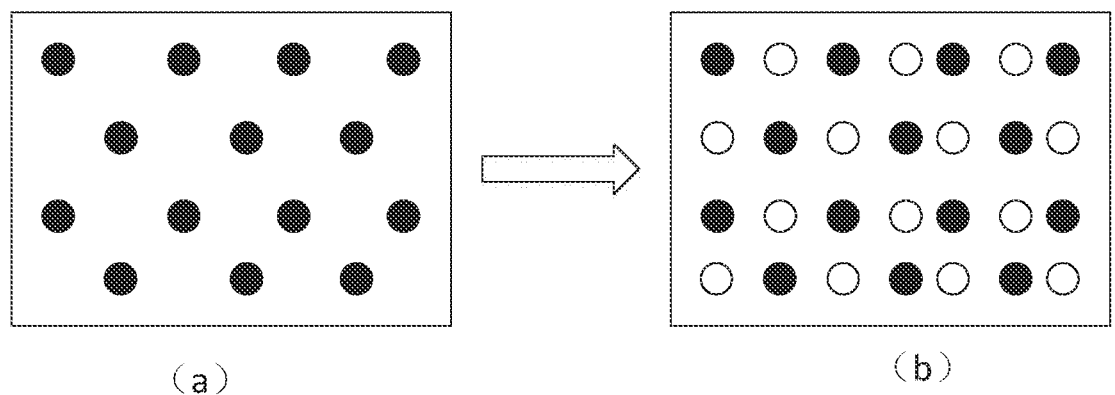
FIG. 3 is a schematic diagram of the distribution of scattered sampling points before and after interpolation according to some embodiments of the present disclosure.

Since vacancies exist between the barrier posts (referring to areas where no barrier posts are arranged), after the scattered sampling points corresponding to the barrier posts in the projection image are obtained, a vacancy between every adjacent scattered sampling points is interpolated based on scattered signals of the scattered sampling points to obtain interpolated sampling points. FIG. 3 is a schematic diagram of the distribution of scattered sampling points before and after interpolation according to some embodiments of the present disclosure. As shown in FIG. 3, picture (a) in FIG. 3 is a projection image formed by rays passing through the barrier array plate 300, and points in picture (a) represent scattered sampling points corresponding to the barrier posts. After the vacancy between every adjacent scattered sampling points is interpolated, the image shown in picture (b) in FIG. 2 is obtained, and points in picture (b) include scattered sampling points (black dots) and interpolated sampling points (white dots), where the scattered sampling points and the interpolated sampling points form a rectangular array.

In the embodiments, since vacancies exist between the barrier posts, to interpolate the vacancy between every adjacent scattered sampling points is to complement a vacant value between every adjacent scattered sampling points. In order to improve the accuracy of determining the scattering of rays, after the interpolated sampling points are obtained, it is still necessary to determine the distribution of scattered signals between the scattered sampling points and the interpolated sampling points (i.e., scattered signals in areas between the scattered sampling points and the interpolated sampling points). Therefore, after the interpolated sampling points are obtained, it is still necessary to determine the distribution of scattered signals between the scattered sampling points and the interpolated sampling points based on the scattered signals of the scattered sampling points and of the interpolated sampling points, so as to obtain a scattering distribution map corresponding to the projection image.

During the determination of the distribution of the scattered signals between the scattered sampling points and the interpolated sampling points, interpolation is performed between the scattered sampling points and the interpolated sampling points to obtain a scattering distribution map corresponding to the projection image.

According to the imaging system provided by the embodiments, an imaging beam is occluded by arranging a barrier array plate, a vacancy between every adjacent scattered sampling points is interpolated, and then the distribution of the scattered signals in the projection image can be effectively determined based on the scattered signals of the scattered sampling points and of the interpolated sampling points, improving the accuracy of determining the scattering of the rays. In this way, a more accurate image of the object to be detected is obtained based on the scattering.

Due to the occlusion of the barrier posts in the barrier array plate 300, the shaded areas cannot receive the ray signals emitted from the imaging source 200 that are transmitted linearly. Therefore, it is necessary to complement the ray signals in the shaded areas via interpolation. However, since the ray signals emitted by the imaging source 200 are not gradually changing, the more the places are occluded, the more significant the interpolation error will be, which may cause artifacts in the image of the object to be detected which is reconstructed based on the scattering of the ray signals obtained after interpolation.

In the embodiment, the shaded areas in the projection image acquired by the imager 400 are reduced by reducing the number of barrier posts in the irradiation area of the imaging source 200, thereby reducing the interpolation error during the reconstruction of the image.

Figure 4:
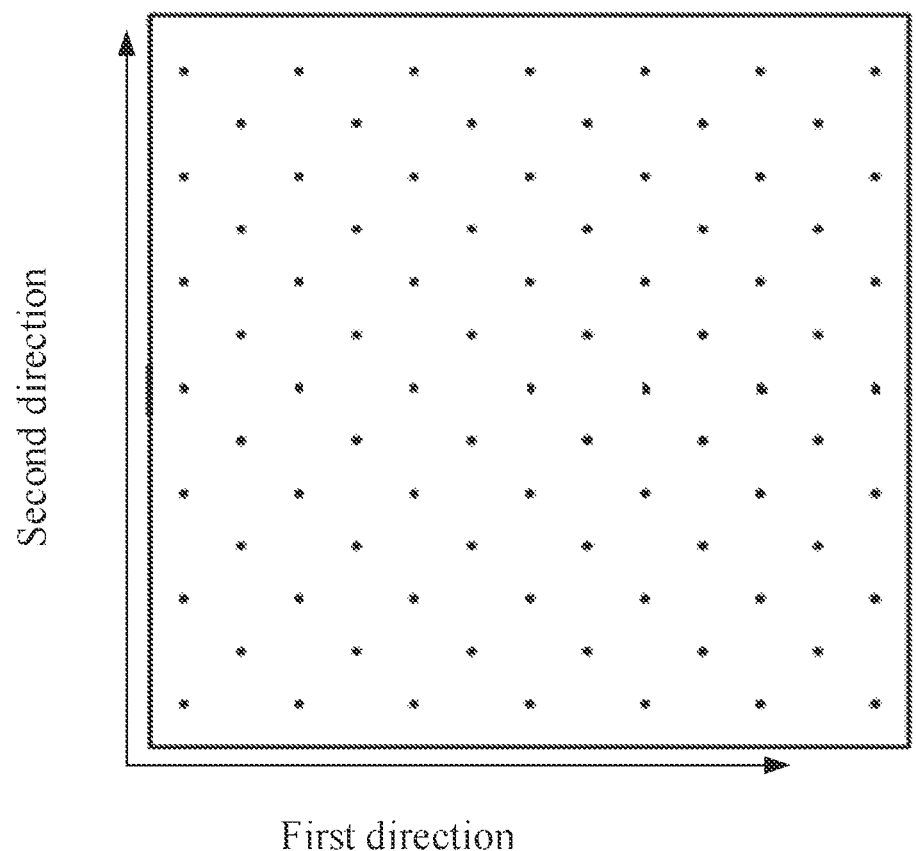
FIG. 4 is a schematic structural diagram of a barrier array plate according to some embodiments of the present disclosure.

FIG. 4 is a schematic structural diagram of a barrier array plate according to some embodiments of the present disclosure. In order to reduce the number of barrier posts in the irradiation area of the imaging source 200 and to facilitate interpolation, as shown in FIG. 4, a plurality of rows of posts are arranged for the barrier array plate in a first direction, and each row of posts includes a plurality of barrier posts arranged in a second direction (the black dots in the figure represent the barrier posts). The barrier posts in two adjacent rows of posts are staggered from each other, and the first direction and the second direction are perpendicular to each other.

The spacing between the rows of posts is the same, and the spacing between the barrier posts included in the rows of posts is also the same. By staggering the barrier posts in two adjacent rows of posts and the first direction and the second direction being perpendicular to each other, a vacancy exists between two adjacent barrier posts in the first direction and the second direction, which can reduce the shaded areas in the projection image. Due to the array distribution of the barrier posts, during the interpolation of the vacancy between the barrier posts, the vacancy between every adjacent barrier posts is interpolated directly in the first direction or the second direction to obtain interpolated sampling points. In this way, it can be ensured that the process of interpolation calculation is more convenient, and the data processing efficiency is higher.

In order to facilitate the control of the number of shaded areas in the projection image, in this embodiment, the imaging system further includes an array plate drive device.

The array plate drive device is arranged on the gantry, and is respectively connected to the barrier array plate 300 and the calibration equipment 100. The array plate drive device is configured to drive the barrier array plate 300 to rotate under the control of the calibration equipment 100.

In the embodiments, the array plate drive device is a motor. The array plate drive device is electrically connected to the calibration equipment 100 and mechanically connected to the barrier array plate 300. When it is necessary to control the barrier array plate 300 to rotate, the calibration equipment 100 sends a rotation command to the array plate drive device, such that the array plate drive device rotates, thereby driving the barrier array plate 300 to rotate. The rotation command includes a rotation angle of the barrier array plate. Upon receiving the rotation command, the array plate drive device can rotate according to the rotation angle included in the rotation command. By way of example, if the rotation angle in the rotation command sent by the calibration equipment is 45°, the array plate drive device drives the barrier array plate to rotate by 45° upon receiving the rotation command.

Figure 5:
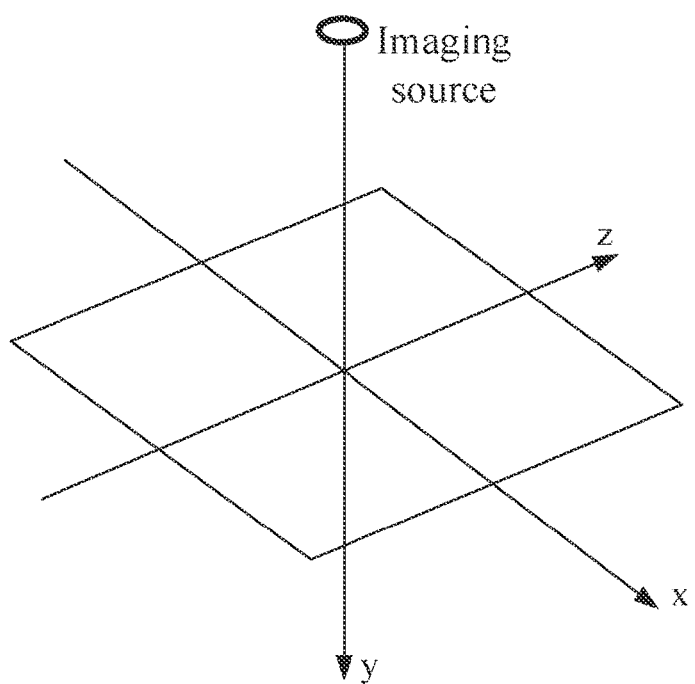
FIG. 5 is a schematic diagram of an irradiation surface of an imaging source according to some embodiments of the present disclosure.

In the embodiments, controlling the barrier array plate 300 to rotate refers to controlling the barrier array plate 300 to rotate within the irradiation surface of the imaging source 200, that is, controlling the barrier array plate 300 to rotate about an axis perpendicular to the irradiation surface of the imaging source 200. FIG. 5 is a schematic diagram of an irradiation surface of the imaging source according to some embodiments of the present disclosure. As shown in FIG. 5, the xz plane is the irradiation surface of the imaging source 200, and the y-axis is an axis perpendicular to the xz plane. Controlling the barrier array plate 300 to rotate in the irradiation surface of the imaging source 200 refers to controlling the barrier array plate 300 to rotate around the y-axis.

In this embodiment, when the barrier array plate 300 is controlled to rotate, an angle may be set to control the barrier array plate 300 to rotate. The angle is set according to actual requirements, which is not limited in this embodiment.

Figure 6:
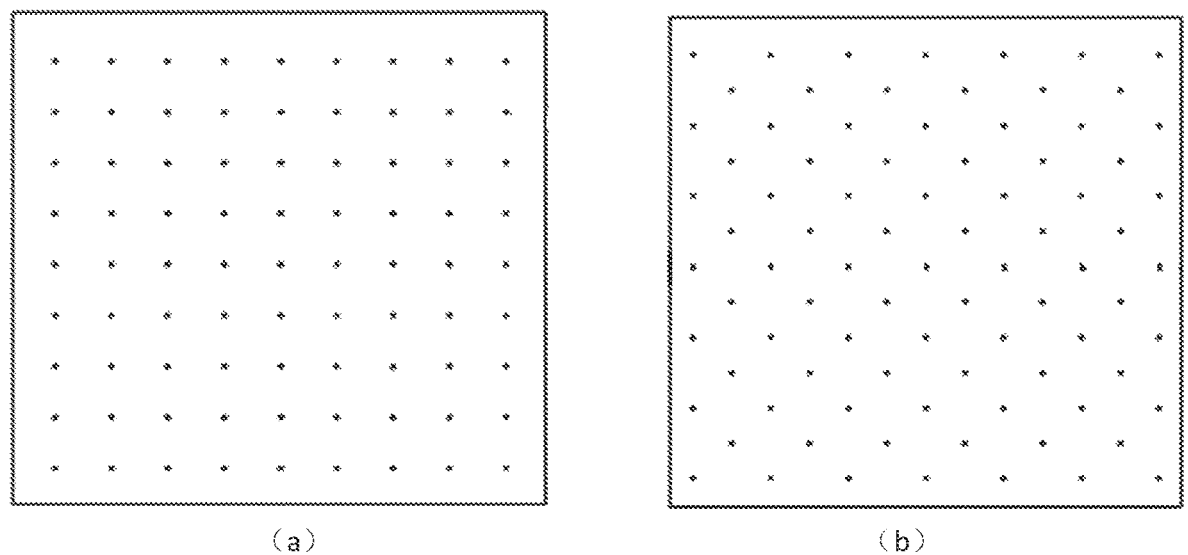
FIG. 6 is a comparison diagram of the barrier array plate before and after rotation according to some embodiments of the present disclosure.

In this embodiment, after the barrier array plate 300 is controlled to rotate, the irradiation area of the imaging source 200 does not change. If the barrier posts in the barrier array plate 300 tilt, the number of barrier posts in the barrier array plate 300 which are located in the irradiation area of the imaging source 200 will reduce and thus the number of shaded areas in the projection image acquired by the imager 400 will reduce. By way of example, FIG. 6 is a comparison diagram of the barrier array plate according to some embodiments of the present disclosure before and after rotation. Picture (a) in FIG. 6 is the barrier array plate not rotated, and picture (b) in FIG. 6 is the barrier array plate rotated by 45°. The barrier posts in the barrier array plate 300 in picture (a) and picture (b) have the same density. In the irradiation area in picture (a), the number of barrier posts in each row is 9, and the number of barrier posts in each column is also 9. After the barrier array plate is rotated by 45°, the barrier posts in the barrier array plate 300 tilt, resulting in that the number of barrier posts in each row and column is reduced from 9 to 6 or 7 (approx. $1/\sqrt{2}$ times). 7 barrier posts exist in odd-numbered rows and odd-numbered columns, and 6 barrier posts in even-numbered rows and even-numbered columns, the position of each barrier post in an even-numbered row is in the middle of two adjacent barrier posts in an odd-numbered row, and the position of each barrier post in an even-numbered column is in the middle of two adjacent barrier posts in an odd-numbered column.

In the embodiments, by controlling the barrier array plate to rotate in the irradiation area of the imaging source, the number of barrier posts in the barrier array plate that are located in the irradiation area of the imaging source can be controlled, thereby reducing the number of shaded areas in the projection image acquired by the imager 400. In this way, by acquiring a projection image formed by the imaging source passing through the rotated barrier array plate on the imager, errors caused by interpolation during image reconstruction based on the projection image can be reduced.

At present, since most of the barrier posts in the barrier array plate are vertically arranged, that is, the barrier posts are parallel to the axis perpendicular to the irradiation surface, and the imaging source emits rays radially, the barrier posts on the edge will occlude excessive pixels in the projection image (i.e., occluding rays that hits an area where the pixels are located, this area may be referred to as a ray-shaded range of the barrier posts, and this area is also the above shaded area), and edge rays passing through the barrier posts have a shorter attenuation path (i.e., rays travelling through the barrier posts have a shorter path). In this way, the barrier posts may not completely occlude the rays, and then the signals in the shaded areas in the projection image may be mixed, reducing the determination accuracy of the scattering of the rays.

Figure 7:
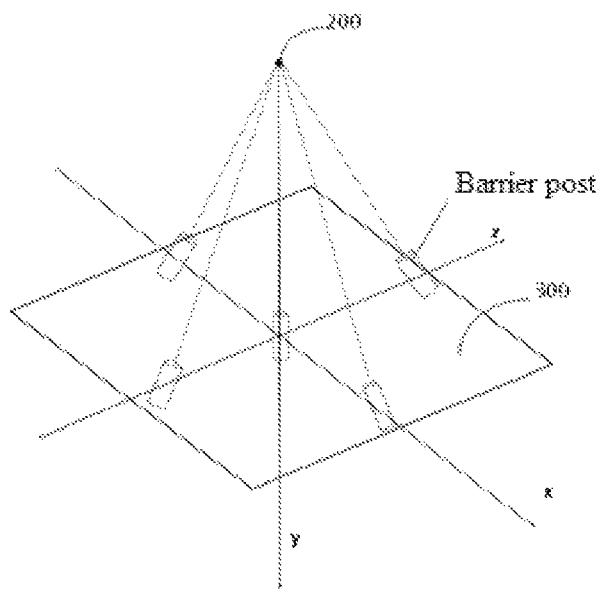
FIG. 7 is a schematic diagram of another structure of the barrier array plate according to some embodiments of the present disclosure.

Based on this, in the embodiments, all the barrier posts in the barrier array plate are arranged towards the imaging source, that is, in the embodiments, an intersection of central axes of the barrier posts is in coincidence with an imaging focal point of the imaging source. FIG. 7 is a schematic diagram of another structure of the barrier array plate according to some embodiments of the present disclosure. As shown in FIG. 7, all the barrier posts in the barrier array plate 300 are arranged towards the imaging source 200, and an intersection of central axes of the barrier posts is in coincidence with an imaging focal point of the imaging source 200. In this way, it is ensured that the barrier posts have consistent ray-shaded ranges, the rays have consistent attenuation paths, and the barrier posts completely occlude the received rays, thereby improving the accuracy of determining the scattering of rays.

In the imaging system according to the embodiments, by controlling the barrier array plate to rotate in the irradiation area of the imaging source, the number of barrier posts in the irradiation area of the imaging source can be reduced, thereby reducing the number of shaded areas in the projection image and reducing errors caused by interpolation during image reconstruction. Moreover, in the embodiments, the intersection of the central axes of the barrier posts is in coincidence with the imaging focal point of the imaging source, which ensures that the barrier posts have consistent ray-shaded ranges, the rays have consistent attenuation paths, and the barrier posts completely occlude the received rays, thereby improving the accuracy of determining the scattering of rays.

Based on the architecture of the above imaging system, some embodiments further provide an image acquisition method, which is applied to the calibration equipment 100 in FIG. 1. The calibration equipment 100 executes the image acquisition method according to the embodiments.

Figure 8:
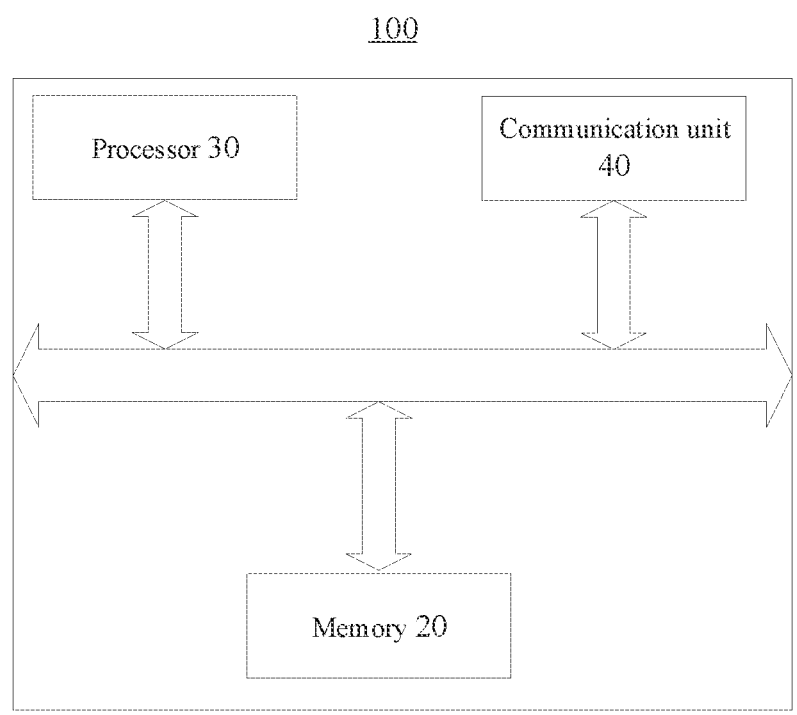
FIG. 8 is a schematic structural diagram of calibration equipment according to some embodiments of the present disclosure.

With reference to FIG. 8, FIG. 8 is a structural block diagram of the calibration equipment 100 according to some embodiments. As shown in FIG. 8, the calibration equipment 100 may include a memory 20, a processor 30, and a communication unit 40. The memory 20 stores machine-readable instructions executable by the processor 30. When the calibration equipment 100 is running, the processor 30 and the memory 20 communicate through a bus, and the processor 30 executes the machine-readable instructions to implement the image acquisition method.

Components of the memory 20, the processor 30, and the communication unit 40 are electrically connected to each other directly or indirectly, so as to realize signal transmission or interaction. By way of example, these components are electrically connected to each other through one or more communication buses or signal lines. The processor 30 is configured to execute executable instructions stored in the memory 20.

The memory 20 is (but is not limited to) random access memory (RAM), read-only memory (ROM), programmable read-only memory (PROM), erasable programmable read-only memory (EPROM), or electric erasable programmable read-only memory (EEPROM), etc.

In some embodiments, the processor 30 is configured to perform one or more functions described in the embodiments. In some embodiments, the processor 30 includes one or more processing cores (e.g., single-core processor(s) or multi-core processor(s)). By way of example, the processor 30 includes a central processing unit (CPU), an application specific integrated circuit (ASIC), an application specific instruction set processor (ASIP), a graphics processing unit (GPU), a physical processing unit (PPU), a digital signal processor (DSP), a field programmable gate array (FPGA), a programmable logic controller (PLC), a microcontroller unit, a reduced instruction set computer (RISC) or a microprocessor, etc., or any combination thereof.

For ease of illustration, only one processor is depicted in the calibration equipment 100. However, it should be noted that the calibration equipment 100 in the embodiments includes a plurality of processors, and therefore the steps performed by one processor described in the embodiments may be performed jointly or independently by the plurality of processors. By way of example, if the processor of the calibration equipment 100 executes step A and step B, it should be understood that step A and step B may be executed jointly by two different processors or independently executed in one processor. By way of example, a first processor performs step A, and a second processor performs step B, or the first processor and the second processor jointly perform steps A and B.

In the embodiments, the memory 20 is configured to store a program, and the processor 30 is configured to execute the program upon receiving an execution instruction. The method defined by the flow process disclosed in any implementation of this embodiment may be applied to the processor 30 or implemented by the processor 30.

The communication unit 40 is configured to establish a communication connection between the calibration equipment 100 and other devices over network, and is configured to send and receive data over network.

In some embodiments, the network is any type of wired or wireless network, or a combination thereof. By way of example only, the network includes a wired network, a wireless network, a fiber optic network, a telecommunications network, an intranet, the Internet, a local area network (LAN), a wide area network (WAN), a wireless local area network, (WLAN), a metropolitan area network (MAN), a wide area network (WAN), a public switched telephone network (PSTN), a Bluetooth network, a ZigBee network or a near field communication (NFC), etc., or any combination thereof.

In the embodiments, the calibration equipment 100 are a computer device that directly issues manipulation commands, such as a host computer device.

It should be understood that the structure shown in FIG. 8 is merely for illustration. The calibration equipment 100 may have more or fewer components than shown in FIG. 8, or have a different configuration than that shown in FIG. 8. The components shown in FIG. 8 may be implemented by hardware, software or a combination thereof.

Figure 9:
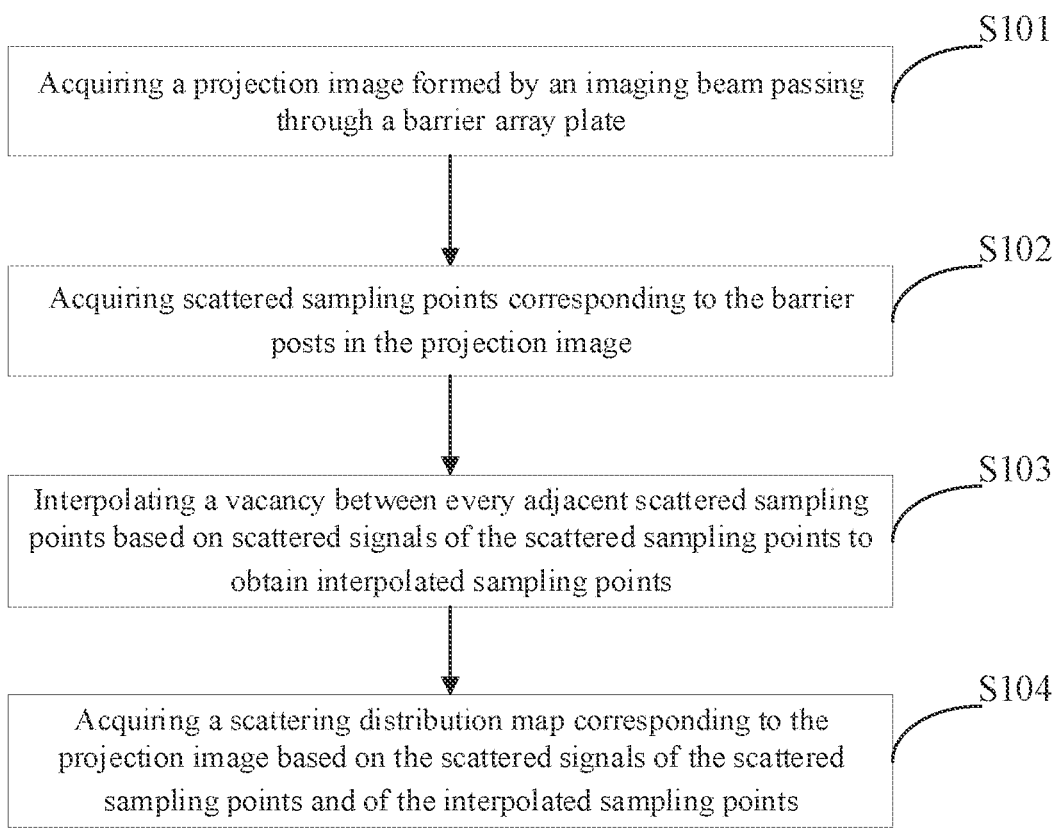
FIG. 9 is a schematic flowchart of an image acquisition method according to some embodiments of the present disclosure.

The steps of the image acquisition method according to the embodiments will be described in detail below based on the structural diagrams shown in FIG. 1 to FIG. 8. FIG. 9 is a schematic flowchart of an image acquisition method according to some embodiments of the present disclosure. With reference to FIG. 9, the image acquisition method according to this embodiment includes step S101 to step S104.

In step S101, a projection image formed by an imaging beam passing through a barrier array plate is acquired.

After an imaging source is turned on, an imaging beam emitted from the imaging source passes through a barrier array plate and is irradiated onto an imager, and the imager receives the imaging beam passing through the barrier array plate and obtains projection data based on the received imaging beam. Calibration equipment obtains a projection image by acquiring the projection data of the imager.

In step S102, scattered sampling points corresponding to barrier posts in the projection image are obtained.

During imaging, rays emitted by the imaging source are occluded by the barrier posts in the barrier array plate, and then shaded areas that are occluded by the barrier posts exist in the projection image acquired by the calibration equipment.

In the embodiments, all barrier posts are arranged towards the imaging source, and an intersection of central axes of the barrier posts is in coincidence with an imaging focal point of the imaging source. In this way, it is ensured that the barrier posts have consistent ray-shaded ranges, the rays have consistent attenuation paths, and the barrier posts completely occlude the received rays, thereby improving the accuracy of determining the scattering of rays.

In the embodiments, the ray signals received in the shaded areas are considered as the scattered signals formed by the scattering of the ray signals. In the embodiments, information of the shaded areas in the projection image is acquired, and the scattered sampling points corresponding to the barrier posts in the projection image are determined based on the information of the shaded areas. Optionally, the centers of the shaded areas are set as the scattered sampling points.

In step S103, a vacancy between every adjacent scattered sampling points is interpolated based on scattered signals of the scattered sampling points to obtain interpolated sampling points.

Since vacancies exist between the barrier posts, after the scattered sampling points corresponding to the barrier posts in the projection image are obtained, the vacancy between every adjacent scattered sampling points is interpolated based on the scattered signals of the scattered sampling points to obtain interpolated sampling points between the adjacent scattered sampling points.

In the embodiments, after the vacancy between every adjacent scattered sampling points is interpolated, the scattered sampling points and the interpolated sampling points form a rectangular array. As shown in FIG. 3, picture (a) in FIG. 3 is a projection image formed by rays passing through the barrier array plate 300, and points in the picture (a) represent scattered sampling points corresponding to the barrier posts. Picture (b) is an image obtained after interpolation, and points in the picture (b) include scattered sampling points and interpolated sampling points. It can be seen from the picture (b) that the scattered sampling points and the interpolated sampling points form a rectangular array.

Optionally, in the embodiments, spline interpolation, polynomial interpolation, linear interpolation or Lagrangian polynomial interpolation may be adopted to interpolate the vacancy between every adjacent scattered sampling points, which is not limited in this embodiment. Since the distribution of the scattered signals in the projection image has a low-frequency characteristic, in some embodiments, a spline interpolation method is selected for interpolation. Optionally, in some embodiments, a cubic spline interpolation method is adopted to interpolate the vacancy between every adjacent scattered sampling points.

In step S104, a scattering distribution map corresponding to the projection image is acquired based on the scattered signals of the scattered sampling points and of the interpolated sampling points.

In the embodiments, since vacancies exist between the barrier posts, to interpolate a vacancy between every adjacent scattered sampling points is to complement a vacant value between every adjacent scattered sampling points. In order to improve the accuracy of the determination of the ray scattering situation, after the vacant value between every adjacent scattered sampling points is complemented to obtain the interpolated sampling points, it is still necessary to determine the distribution of the scattered signals between the scattered sampling points and the interpolated sampling points. Optionally, after the interpolated sampling points are obtained, interpolation is performed between the scattered sampling points and the interpolated sampling points based on the scattered signals of the scattered sampling points and of the interpolated sampling points to obtain the distribution of the scattered signals between the scattered sampling points and the interpolated sampling points, so as to obtain the scattering distribution map corresponding to the projection image.

Interpolation methods such as spline interpolation, polynomial interpolation, linear interpolation or Lagrange polynomial interpolation may be adopted to perform interpolation between the scattered sampling points and the interpolated sampling points, which is not limited in the embodiments. Optionally, in the embodiments, a cubic spline interpolation method is adopted to perform interpolation between the scattered sampling points and the interpolated sampling points.

In the image acquisition method according to the embodiments, an imaging beam is occluded by arranging a barrier array plate, a vacancy between every adjacent scattered sampling points is interpolated, and then the distribution of the scattered signals in the projection image can be effectively determined based on the scattered signals of the scattered sampling points and of the interpolated sampling points, thereby improving the accuracy of determining the scattering of the rays forming the projection image.

When the object to be detected is being scanned, the object to be detected itself will also scatter the imaging beam, affecting the confirmation of the scattered sampling points. By way of example, during the determination of the scattered sampling points in the projection image, scattering points formed in the projection image after the rays are scattered on the object to be detected are taken as scattered sampling points. In order to improve the accuracy of determining the scattering of the rays, in the embodiments, projection images are acquired in the case that the object to be detected is placed and when no object to be detected is placed. Therefore, the projection image in the embodiments includes a first image and a second image. The first image is a projection image formed when no object to be detected is placed. The second image is a projection image formed when an object to be detected is placed.

During the acquisition of the first image, after the imaging source is turned on, the calibration equipment directly acquires the first image formed by the imaging beam emitted from the imaging source passing through the barrier array plate. During the acquisition of the second image, the object to be detected is placed in the irradiation surface of the imaging source first, and then after the imaging source is turned on, the imaging source scans the object to be detected through the barrier array plate, and then the calibration equipment acquires the second image through the imager.

After the first image and the second image are acquired, the scattered sampling points corresponding to the barrier posts are obtained based on the first image and the second image. Optionally, it may be obtained by the following steps:

center points of shaded areas that are occluded by the barrier posts in the first image are obtained; and target points corresponding to the center points of the shaded areas in the second image are obtained based on the center points of the shaded areas, and the target points are taken as scattered sampling points in the second image. The target points are scattered sampling points corresponding to the barrier posts.

Since the position of the barrier array plate does not change during the acquisition of the first image and the second image, the shaded areas in the first image and the second image are the same. Since the first image is a projection image acquired in the case that no object to be detected is placed and the second image is a projection image acquired in the case that the object to be detected is placed, the scattered signals of the shaded areas that are occluded by the barrier posts in the first image are scattered signals generated by the imaging beam emitted by the imaging source scattering on the barrier array plate, and the scattered signals of the shaded areas that are occluded by the barrier posts in the second image include scattered signals generated when the imaging source passes through the object to be detected and scatters on the same.

In order to accurately acquire the scattered sampling points of the projection image, in the embodiments, center points of the shaded areas that are occluded by the barrier posts in the first image are obtained first; then target points corresponding to the center points of the shaded areas in the second image (i.e., target points at the same position as the center points of the shaded areas) are obtained based on the center points of the shaded areas, and the target points are taken as the scattered sampling points in the second image.

In order to improve the accuracy, the center points of the shaded areas that are occluded by the barrier posts in the first image may be obtained by the following steps:

(1) Pixels in the first image are parsed to determine shaded pixels corresponding to the shaded areas that are occluded by the barrier posts.

(2) The center points of the shaded areas that are occluded by the barrier posts in the first image are determined based on the shaded pixels.

The pixels in the first image being parsed to determine the shaded pixels corresponding to the shaded areas that are occluded by the barrier posts includes sorting each pixel in the first image based on a set projection threshold to obtain the shaded pixels corresponding to the shaded areas that are occluded by the barrier posts in the first image.

Optionally, the projection threshold is set in consideration of penumbra effect and noise influence. In the embodiments, sorting each pixel in the first image based on the projection threshold includes setting pixels whose pixel value is smaller than the projection threshold as shaded pixels that are occluded, that is, belonging to shaded pixels corresponding to the shaded areas; and setting pixels whose pixel values are not smaller than the projection threshold as pixels that are not occluded, that is, not belonging to shaded pixels corresponding to the shaded areas. In order to distinguish between shaded pixels that are occluded and pixels that are not occluded, the pixel values of the shaded pixels that are occluded may be set to 0, and the pixel values of the pixels that are not occluded may be set to 1.

In an optional implementation, for shaded pixels that are occluded, a first flag may be set; and for pixels that are not occluded, a second flag may be set. The first flag and the second flag may be any kind of flag symbols, such as numbers, letters, or character strings, etc., which is not limited, as long as they can be distinguished. By way of example, for shaded pixels that are occluded, the first flag may be set to 0; and for pixels that are not occluded, the second flag may be set to 1.

After the shaded pixels in the first image are obtained, the center points of the shaded areas that are occluded by the barrier posts in the first image are determined based on the shaded pixels in the first image.

Determining the center points of the shaded areas that are occluded by the barrier posts in the first image based on the shaded pixels in the first image includes finding connected areas of the shaded pixels in the first image and then determining the connected areas as shaded areas that are occluded by the barrier posts.

Finding the connected areas of the shaded pixels in the first image includes for each shaded pixel, searching for a connected area of the shaded pixel in a set neighborhood. The set neighborhood may be 8 neighborhoods or 4 neighborhoods, etc., which is not limited.

By way of example, if the connected area is searched in the form of 8 neighbors, then for each shaded pixel, whether flags of pixels in 8 directions of up, down, left, right, upper left, upper right, lower left, and lower right where the shaded pixel is located is the first flag, that is, whether it is the same as the flag of the shaded pixel; then pixels having the first flag are classified into the same connected area; and so on, until the connected areas of all shaded pixels are found. Alternatively, for each shaded pixel, whether values of pixels in 8 directions of up, down, left, right, upper left, upper right, lower left, and lower right where the shaded pixel is located is 0, that is, whether it is the same as the value of the shaded pixel; then pixels with values of 0 are classified into the same connected area; and so on, until the connected areas of all shaded pixels are found.

If the connected area is searched in the way of 4 neighborhoods, then for each shaded pixel, whether flags of pixels in 4 directions of up, down, left and right where the shaded pixel is located is the first flag; and then pixels having the first flag are classified into the same connected area; and so on until the connected areas of all shaded pixels are found. Alternatively, for each shaded pixel, whether value of pixels in 4 directions of up, down, left and right where the shaded pixel is located is 0, that is, whether it is the same as the value of the shaded pixel; then pixels with values of 0 are classified into the same connected area; and so on until the connected areas of all shaded pixels are found.

It can be understood that each connected area found corresponds to one shaded area that is occluded by the barrier post. After the shaded areas that are occluded by the barrier posts in the first image are found, the center points of the shaded areas that are occluded by the barrier posts in the first image may be determined.

It can be understood that the center points of the shaded areas that are occluded by the barrier posts in the first image are the scattered sampling points in the first image. Since the shaded areas in the first image are the same as the shaded areas in the second image, after the center points of the shaded areas that are occluded by the barrier posts in the first image are determined, target points corresponding to the center points of the shaded areas in the second image may be obtained based on the center points of the shaded areas.

Acquiring the target points corresponding to the center points of the shaded areas in the second image based on the center points of the shaded areas includes finding positions in the second image the same as the positions of the center points in the first image and then taking the found positions as the positions of the target points, so as to determine the scattered sampling points in the second image. By way of example, if the position of a certain center point in the first image is the position of row A and column B, then the position of row A and column B is found in the second image, and a point at the position of row A and column B in the second image is taken as a target point corresponding to the center point.

After the target points in the second image are obtained, the scattered sampling points in the second image are obtained.

After the scattered sampling points in the first image and in the second image are obtained, scattered signals of the scattered sampling points are determined. In the embodiments, ray signals of the scattered sampling points are directly determined as the scattered signals of the scattered sampling points. However, since it is generally difficult to ensure that the barrier posts completely occlude the received ray signals and there may be other factors in the imaging system that affect the transmission of the rays, the ray signals directed to the shaded areas of the projection image include some other interference signals in addition to the scattered ray signals. In the embodiments, more accurate scattered signals are determined by correcting the ray signals of the scattered sampling points.

In an exemplary embodiment, the scattered signals of the scattered sampling points may be determined in the following steps s1, s2, and s3:

In step s1, ray signals of the scattered sampling points are obtained. For example, the pixel value of each scattered sampling point in the projection image, that is, the value of the ray signal of each scattered sampling point, may be obtained.

In step s2, equivalent water thicknesses of the scattered sampling points are determined based on ray signals of points around the shaded areas where the scattered sampling points are located in the projection image.

In the embodiments, the attenuation of the ray signals during transmission in water is taken as a reference to show the attenuation of the ray signals during the process of forming the projection image. By way of example, a space in which the ray signals that form the scattered sampling points in the projection image are transmitted in the imaging system is equivalent to water of a certain thickness, and the thickness is an equivalent water thickness of the space. In the embodiments, for the convenience of description, the equivalent water thickness of this space is referred to as the equivalent water thickness of the scattered sampling point, so the equivalent water thickness of the scattered sampling point means the thickness of water that the ray signals must pass through for the same degree of attenuation as the scattered sampling point when not occluded by the barrier post. The attenuation of the ray signals at the scattered sampling point is the same as the attenuation of the ray signals in the imaging beam in water of this equivalent water thickness.

In the embodiments, the projection image includes a first image and a second image. The first image and the second image are acquired first. For each of the scattered sampling points, a ray signal of at least one point around a shaded area where the scattered sampling point is located is determined in the first image and the second image respectively, and the at least one point is located in an area in the image that is not occluded by the barrier post (this area is referred to as a target area below). Next, for each scattered sampling point, an equivalent water thickness of the scattered sampling point is determined based on the ray signal of the at least one point in the first image and the second image respectively. Since the scattered sampling point is occluded by the barrier post, the attenuation of the ray signal due to interference cannot be determined based on the ray signal of the scattered sampling point, and accordingly the equivalent water thickness of the scattered sampling point cannot be directly determined, in this embodiment, the equivalent water thickness of the scattered sampling point is estimated by using the equivalent water thickness of the point in the target area around the scattered sampling point.

In an exemplary embodiment, the at least one point includes a point closest to the scattered sampling point in the target area around the scattered sampling point. When the number of this point is 1, the equivalent water thickness of this point is directly determined as the equivalent water thickness of the scattered sampling point. If a plurality of points exist, an average value, a median value or a value obtained through other processing (such as smoothing) of the equivalent water thicknesses of the plurality of points may be taken as the equivalent water thickness of the scattered sampling point. Optionally, the plurality of points may be respectively located in different directions around the scattered sampling point. If the number of the points is 4, the 4 points are points closest to the scattered sampling point that are located in the target area in four directions of up, down, left, and right of the scattered sampling point. Selecting a plurality of points in different directions for calculation can ensure high accuracy of the equivalent water thickness of the determined scattered sampling point.

The equivalent water thickness of any point in the projection image is $$T = \frac{-\ln\left(\frac{x_2}{x_1}\right)}{u};$$

where $x_2$ represents a value of a ray signal of a point in the second image, $x_1$ represents a value of a ray signal of a point in the first image, and u represents a water linear attenuation coefficient. u may be 0.206/cm (per centimeter), which is a water linear attenuation coefficient corresponding to a ray signal with energy of 60 keV (kiloelectron volt). In the embodiments, the scattered signal or ray signal of each point in the projection image has a corresponding value, and a value of a signal of a certain point in the projection image may refer to a pixel value of the point.

In step s3, the scattered signals of the scattered sampling points are acquired by correcting the ray signals of the scattered sampling points based on a correction ratio corresponding to the equivalent water thicknesses of the scattered sampling points. The correction ratio is positively correlated to the equivalent water thickness.

In an exemplary embodiment, a set correlation between water thickness and a correction ratio is acquired first. The correction ratio represents the proportion of the interference signal in the ray signal, and the correction ratio is negatively related to the proportion of the interference signal in the ray signal. The correction ratio is a value less than or equal to 1. In the correlation, the correction ratio is positively correlated with the water thickness. The correlation is a correlation table of a plurality of water thicknesses and correction ratios. Afterwards, according to the correlation, a correction ratio corresponding to the equivalent water thickness of each of the scattered sampling points may be determined. Next, according to the correction ratio corresponding to the equivalent water thickness of each of the scattered sampling points, the ray signal of the scattered sampling point is corrected to obtain the scattered signal of each of the scattered sampling points. By way of example, a product of the value of the ray signal of the scattered sampling point and the corresponding correction ratio is determined as the value of the scattered signal of the scattered sampling point.

Optionally, the scattered signals of the scattered sampling points are determined in other ways based on the equivalent water thicknesses of the scattered sampling points. By way of example, the equivalent water thickness is calculated to obtain the amount of interference signal in the ray signal of the scattered sampling point, and then the value of the interference signal is subtracted from the value of the ray signal of the scattered sampling point to obtain the value of the scattered signal.

In the embodiments, after the scattered signals of the scattered sampling points are determined, interpolation is performed based on the scattered signals of the scattered sampling points to obtain interpolated sampling points. Since the second image is a projection image formed in the case that an object to be detected is placed and the first image is a projection image formed in the case that no object to be detected is placed, in order to reduce the amount of calculation, only the second image is interpolated. In this way, the scattered sample points for interpolation are the target points in the second image.

In the embodiments, interpolation is performed only based on the scattered signal of the scattered sampling point itself. Alternatively, interpolation is performed taking into account the scatted signals of the scatted sampling points and of other points around them. For example, the step of interpolating the vacancy between every adjacent scattered sampling points to obtain the interpolated sampling points based on the scattered signals of the scattered sampling points includes:

acquiring scattered signals of set pixel ranges where the scattered sampling points are located, the set pixel range being an area in the projection image;

interpolating the vacancy between every adjacent scattered sampling points based on the scattered signals of the set pixel ranges where the scattered sampling points are located to obtain the interpolated sampling points.

The set pixel range may be set according to actual needs, which is not limited, such as a pixel range of m*n, where m and n are positive integers. By way of example, the scattered sampling point is a center point within the set pixel range where it is located. An average value or median value of the scattered signals of the set pixel range may refer to an average value or median value of the scattered signals of the pixel points within the set pixel range.

Interpolating the vacancy between every adjacent scattered sampling points based on the scattered signals of the set pixel ranges where the scattered sampling points are located may include calculating an average value or median value of the scattered signals of the set pixel ranges where the adjacent scattered sampling points are located, and interpolating the vacancy between the adjacent scattered sampling points based on the average value or median value to obtain the interpolated sampling points. Alternatively, a smoothing method such as Gaussian filtering or bilateral filtering is adopted for the scattered signals of the set pixel ranges where the scattered sampling points are located to obtain smoothed values; and interpolating the vacancy between every adjacent scattered sampling points based on the scattered signals of the set pixel ranges where the scattered sampling points are located refer to interpolating the vacancy between every adjacent scattered sampling points based on the smoothed values.

In the embodiments, the method of determining a scattered signal of a point other than the scattered sampling point (such as an auxiliary point) within the set pixel range may be the same as that of the scattered sampling point. By way of example, an equivalent water thickness may be determined for each auxiliary point, and then a correction ratio corresponding to the auxiliary point may be determined, and a scattered signal of the auxiliary point may be determined based on the correction ratio.

Optionally, instead of separately determining the correction ratio for the auxiliary point, a ray signal of the auxiliary point is corrected using the correction ratio corresponding to the scattered sampling point to determine a scattered signal of the auxiliary point. In the manners, the average value of the scattered signals of the set pixel range is a product of the average value of the scattered signals of the set pixel range and the correction ratio of the scattered sampling point. By way of example, instead of first determining the scattered signals of the points within the set pixel range, an average value of the ray signals of the points within the set pixel range may be determined first. Then, the average value of the scattered signals of the points within the set pixel range may be directly determined based on the correction ratios of the scattered sampling points, so as to perform interpolation based on the average value of the scattered signals.

In the embodiments, compared the case that the ray signal of the scattered sampling point is corrected to obtain the scattered signal with the case that the ray signal of the scattered sampling point is directly determined as the scattered signal, the set pixel range where the scattered sampling point is located may be the same or may also be different, which is not limited in the embodiments of the present disclosure.

In the embodiments, as shown in FIG. 4, the barrier array plate is provided with a plurality of rows of posts in a first direction, and each row of posts includes a plurality of barrier posts arranged in a second direction. The barrier posts in two adjacent rows of posts are staggered from each other, and the first direction and the second direction are perpendicular. The first direction and the second direction may correspond to the orientation of the human body when the imaging beam scans the human body. By way of example, the second direction is parallel to the head and foot direction of the human body (i.e., length direction of bed), and the first direction is parallel to the left-right direction of the human body (i.e., width direction of bed).

The spacing between the rows of posts is the same, and the spacing of the barrier posts included in the rows of posts is also the same. By staggering the barrier posts in two adjacent rows of posts the first direction and the second direction being perpendicular, staggered vacancies exist between two adjacent barrier posts in the first direction and the second direction, which can reduce the shaded areas in the projection image. At the same time, due to the array distribution of the barrier posts, interpolating the vacancy between the barrier posts includes interpolating the vacancy between every adjacent barrier posts directly in the first direction or the second direction to obtain the interpolated sampling points, which can ensure that the process of interpolation is more convenient, and the data processing efficiency is high.

Interpolating the vacancy between every adjacent barrier posts in the first direction or the second direction belongs to one-dimensional interpolation. Therefore, an interpolation direction may be firstly determined from the first direction and the second direction, and then in the interpolation direction, the vacancy between every adjacent scattered sampling points in the projection image may be interpolated based on an average value, median value or smoothed value of scattered signals of set pixel ranges where the scattered sampling points are located. Optionally, the first direction or the second direction may be set as a default interpolation direction, and each vacancy in the projection image may be interpolated in the default interpolation direction based on scattered signals of adjacent scattered sampling points.

Figure 10:
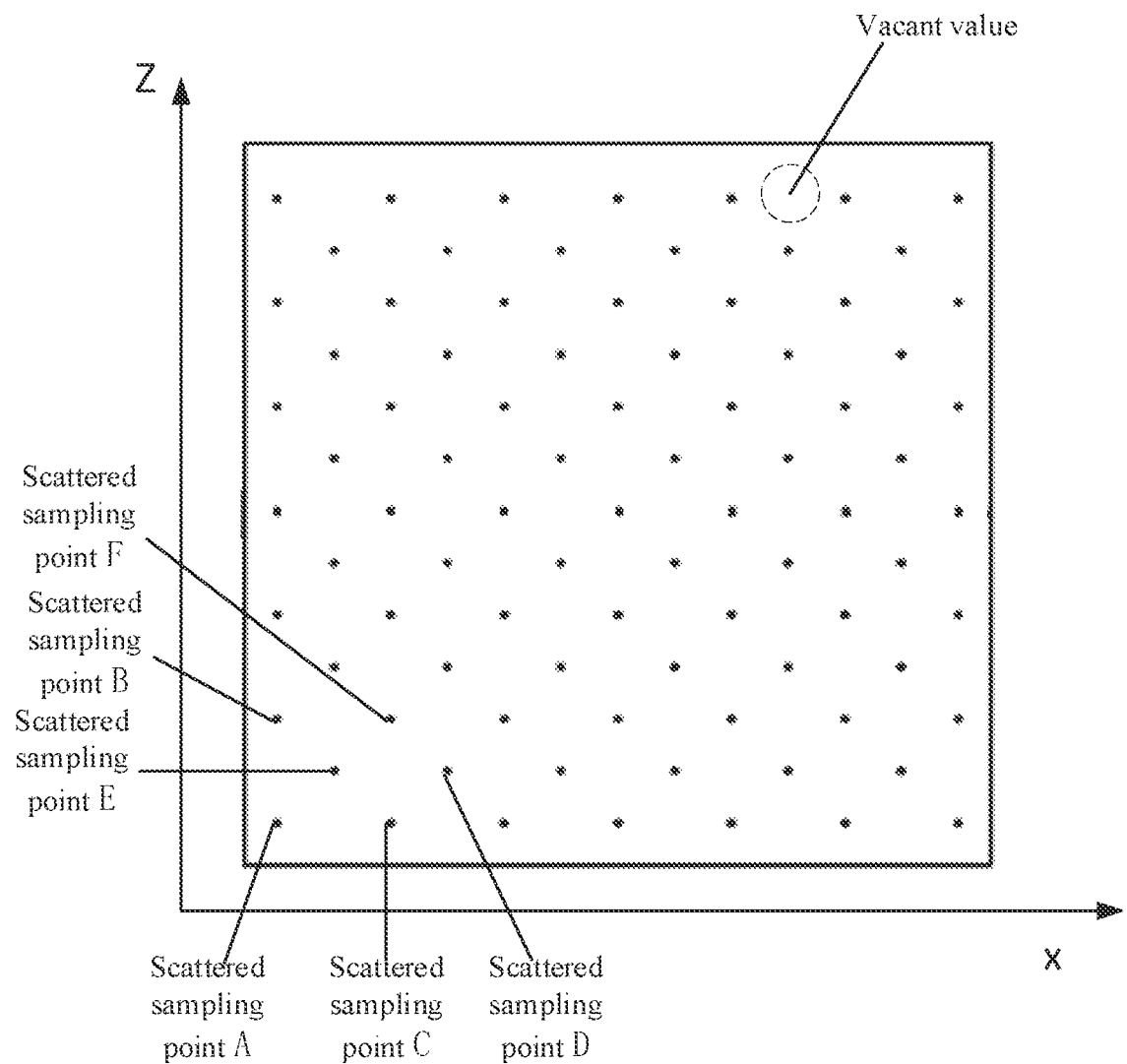
FIG. 10 is a schematic diagram of a projection image according to some embodiments of the present disclosure.
Figure 11:
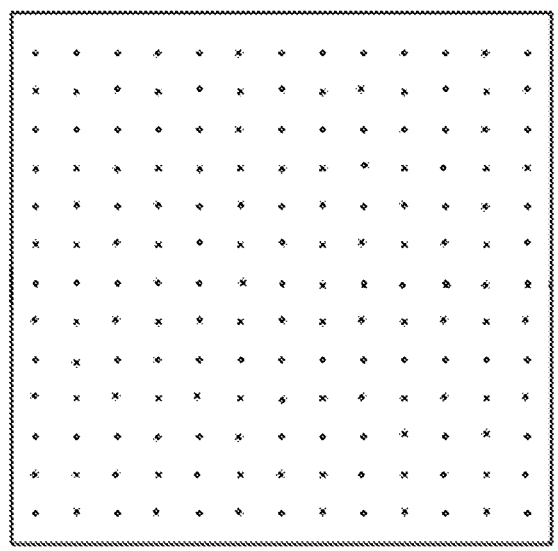
FIG. 11 is a diagram of grid sampling points according to some embodiments of the present disclosure.

By way of example, FIG. 10 is a schematic diagram of a projection image according to some embodiments of the present disclosure. As shown in FIG. 10, the Z-axis (second direction) is set as the interpolation direction, and the average value is set for interpolation. Interpolation is performed between a scattered sampling point A and a scattered sampling point B based on an average value of scattered signals of a set pixel range where the scattered sampling point A is located and an average value of scattered signals of a set pixel range where the scattered sampling point B is located. For the sampling point diagram shown in FIG. 10, after interpolation is performed between every adjacent scattered sampling points in the Z-axis direction, the 13×13 grid sampling point diagram shown in FIG. 11 may be obtained.

In the embodiments, for each vacancy in the projection image, interpolation can be performed on the vacancy based only on the scattered signal of the scattered sampling points around the vacancy in the default interpolation direction. In FIG. 10, only the scattered signals of two adjacent scattered sampling points along the Z-axis are used to interpolate the vacancy between the two scattered sampling points. Interpolating between two points based on their signals can be called interpolation. Optionally, there may be a vacancy with adjacent scattered sampling points on only one side of the default interpolation direction. In this case, interpolation can only be carried out based on the scattered signal of the scattered sampling point. Such interpolation method can be called extrapolation.

In the embodiments, it is also possible to interpolate an vacancy based on scattered signals of multiple scattered sampling points in different directions. For example, a vacancy can be interpolated based on all adjacent scattered sampling points located on either side of the vacancy in the first and second directions. As shown in FIG. 10, the vacancy among scattered sampling points C, D, E and F can be interpolated according to the scattered signals of scattered sampling points C, D, E and F.

For example, in the projected image, two auxiliary sampling points are obtained by interpolating the space between every adjacent scattered sampling points in the first and second directions respectively. One of the auxiliary sampling points corresponds to the first direction and the other to the second direction. The interpolated sampling point at the vacancy is then determined based on the two auxiliary sampling points. In the embodiments, a vacancy being interpolated in a direct means that the vacancy is interpolated based on the scattered signal of scattered sampling points around the vacancy in that direction. The auxiliary sampling points corresponding to a certain direction are the points obtained by interpolation in accordance with the direction For a vacancy to be interpolated in the projection image, interpolation in different interpolation directions will result in different interpolation results. In the embodiments, one of the two auxiliary sampling points is selected as the interpolated sampling point. For example, the auxiliary sampling point corresponding to the target direction in the first direction and the second direction can be used as the interpolated sampling point, that is, choosing one direction from the first direction and the second direction as the interpolation direction for acquiring the interpolated sampling point. Optionally, the scattered signals of the two auxiliary sampling points can also be processed (such as weighted average processing) to a certain extent to obtain the scattered signals of the interpolated sampling points.

For a vacancy with adjacent scattered sampling points on both sides in only one direction (such as a vacancy at the edge in the projection image) of the first direction or the second direction, the vacancy is interpolated based on scattered signals of adjacent scattered sampling points in this direction, and the direction is the target direction. By way of example, for a vacancy between the scattered sampling point A and the scattered sampling point B in FIG. 10, the Z direction is taken as the interpolation direction; and for a vacancy between the scattered sampling point A and the scattered sampling point C, the x direction is taken as the interpolation direction. In this way, interpolation is preferred. The interpolation is based on more information, which makes interpolation results more accurate.

For a vacancy with adjacent scattered sampling points on both sides in the first direction and the second direction, a more suitable interpolation direction (hereinafter referred to as a target direction) may be selected for it to obtain a more accurate result after interpolation. As shown in FIG. 10, for a vacancy between the scattered sampling points C, D, E and F, the scattered sampling points C and F are adjacent scattered sampling points of the vacancy on both sides in the Z-axis direction, and the scattered sampling points D and E are adjacent scattered sampling points of the vacancy on both sides in the x-axis direction. During interpolation of the vacancy, an appropriate interpolation direction is selected from the Z-axis direction and the X-axis direction.

In the embodiments, differences between scattered signals of adjacent scattered sampling points of a vacancy on both sides in the first direction and the second direction and interpolated values obtained by taking these two directions as the interpolation direction may be determined respectively. The target direction is determined based on the differences and the interpolated results (i.e., auxiliary sampling points as determined above).

By way of example, in the first direction and the second direction, the target direction satisfies at least one of: an absolute value of a difference value between scattered signals of two adjacent scattered sampling points of a vacancy on both sides in the target direction being small, and a value obtained by interpolation based on the scattered signals of the two scattered sampling points in the target direction being small. The absolute value of the difference value being small indicates that the difference between the scattered signals of the two scattered sampling points is small. Since the scattered signals change slowly in the projection image, the result obtained by interpolation based on the scattered signals with a small difference can be more accurate. In addition, it is safer to select a small interpolation result to ensure the normal display of a subsequent image corrected based on the interpolation result, and to avoid the risk that the corrected image cannot be displayed due to over-correction.

In some embodiments, whether the default interpolation direction (e.g., second direction) satisfies the above conditions (e.g., target condition) required by the target direction may be determined. The target direction is the second direction in the case that the second direction satisfies a target condition, or the target direction is the first direction in the case that the second direction does not satisfy the target condition. The target condition includes at least one of: in the first direction and the second direction, an absolute value of a difference value between the scattered signals of the two scattered sampling points on two sides of the vacancy in the second direction being minimum, or a value obtained by interpolating the vacancy based on the scattered signals of the two scattered sampling points in the second direction being minimum (i.e., a value of the scattered signal of the auxiliary sampling point corresponding to the second direction being minimum).

As shown in FIG. 10, the default interpolation direction is the Z-axis direction (i.e., the second direction). Interpolating the vacancy between the scattered sampling points C, D, E and F may include first determining whether an absolute value of a difference value between the scattered signals of the scattered sampling points C and F (hereinafter referred to as a first absolute value) is smaller than an absolute value of a difference value between the scattered signals of the scattered sampling points D and E (hereinafter referred to as a second absolute value).

If the first absolute value is smaller than the second absolute value, then the Z-axis direction is taken as the interpolation direction. If the first absolute value is greater than or equal to the second absolute value, whether an interpolation result (hereinafter referred to as a first result) obtained by interpolation based on the scattered signals of the scattered sampling points C and F is smaller than an interpolation result (hereinafter referred to as a second result) obtained by interpolation based on the scattered signals of the scattered sampling points D and E is determined. Optionally, the first result is equal to an average value of the scattered signals of the scattered sampling points C and F, and the second result is equal to an average value of the scattered signals of the scattered sampling points D and E.

If the first result is smaller than the second result, the Z-axis direction is taken as the interpolation direction. If the first result is greater than the second result, the X-axis direction is taken as the interpolation direction. If the first result is equal to the second result, either of the Z-axis direction and the x direction is taken as the interpolation direction.

Optionally, one-dimensional cubic spline interpolation may be adopted for interpolation between every adjacent scattered sampling points in the interpolation direction based on an average value, median value or smoothed value of scattered signals in set pixel ranges where the scattered sampling points are located.

Through the above process, interpolated sampling points between every adjacent scattered sampling points are obtained after the vacancy between every adjacent scattered sampling points is interpolated. To interpolate the vacancy between every adjacent scattered sampling points is to complement the vacant value between every adjacent scattered sampling points; and in order to improve the accuracy of determining the ray scattering situation, after the vacant value between every adjacent scattered sampling points is interpolated and complemented to obtain the interpolated sampling points, it is still necessary to determine the scattering distribution between the scattered sampling points and the interpolated sampling points. Therefore, after the interpolated sampling points are obtained, it is still necessary to acquire the distribution of scattered signals between the scattered sampling points and the interpolated sampling points based on the scattered signals of the scattered sampling points and of the interpolated sampling points, so as to obtain the scattering distribution map corresponding to the projection image.

Optionally, the step of obtaining the scattering distribution map corresponding to the projection image based on the scattered signals of the scattered sampling points and of the interpolated sampling points may include:

perform interpolation or fitting between the scattered sampling points and the interpolated sampling points based on scattered signals of set pixel ranges where the scattered sampling points are located and scattered signals of the interpolated sampling points to obtain the scattering distribution map.

Perform interpolation or fitting between the scattered sampling points and the interpolated sampling points based on the scattered signals of the set pixel ranges where the scattered sampling points are located and the scattered signals of the interpolated sampling points to obtain the scattering distribution map may include first calculating an average value, median value or smoothed value of the scattered signals of the set pixel ranges where the scattered sampling points are located. Then interpolation or fitting is performed between the scattered sampling points and the interpolated sampling points based on the scattered signals of the interpolated sampling points and the average value, median value or smoothed value of the scattered signals of the set pixel ranges where the scattered sampling points are located to obtain the scattering distribution between the scattered sampling points and the interpolated sampling points, so as to obtain an overall scattering distribution map.

Figure 12:
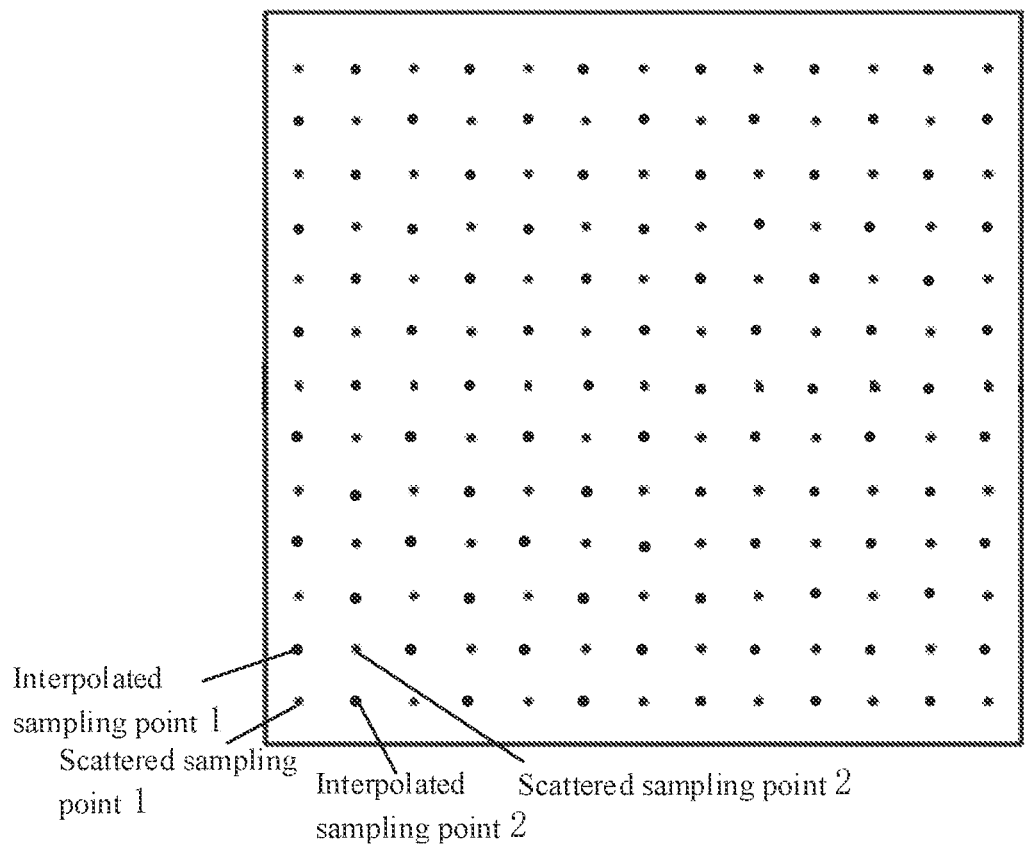
FIG. 12 is a schematic diagram of the distribution of another sampling point according to some embodiments of the present disclosure.

Performing interpolation between the scattered sampling points and the interpolated sampling points based on the scattered signals of the interpolated sampling points and the average value, median value or smoothed value of the scattered signals of the set pixel ranges where the scattered sampling points are located belongs to two-dimensional interpolation. Therefore, during interpolation, values of surrounding adjacent sampling points (i.e., values of adjacent sampling points in the first direction and the second direction, which may be pixel values) should be taken into consideration. By way of example, FIG. 12 is a schematic diagram of another sampling point distribution according to some embodiments of the present disclosure. As shown in FIG. 12, taking the average value as an example, to perform interpolation between a scattered sampling point 1 and an interpolated sampling point 1, it is necessary to take into consideration an average value of scattered signals in a set pixel range where the scattered sampling point 1 is located, a value of a scattered signal of the interpolated sampling point 1, an average value of scattered signals of a set pixel range where a scattered sampling point 2 is located, and a value of a scattered signal of an interpolated sampling point 2.

Optionally, two-dimensional cubic spline interpolation may be adopted for interpolation between the scattered sampling points and the interpolated sampling points, Fitting between the scattered sampling points and the interpolated sampling points based on the scattered signals of the interpolated sampling points and the average value, median value or smoothed value of the scattered signals of the set pixel ranges where the scattered sampling points are located shall be performed based on the signal values of the overall sampling points. To illustrate with the average value, an average value of scattered signals of set pixel ranges where the scattered sampling points are located may be calculated first; then a two-dimensional surface is fitted based on the average value of the scattered signals of the set pixel ranges where the scattered sampled points are located and the signal values of the interpolated sampling points, where the two-dimensional surface represents the distribution of the overall scattered signals in the projection image.

Fitting methods such as polynomial fitting or locally weighted regression fitting may be adopted for fitting, which is not limited herein.

After the distribution of the scattered signals between the scattered sampling points and the interpolated sampling points are determined through the above process, the scattering distribution map corresponding to the projection image may be obtained.

In the image acquisition method according to the embodiments, an imaging beam is occluded by arranging a barrier array plate, a vacancy between every adjacent scattered sampling points is interpolated, and then the distribution of the scattered signals in the projection image can be accurately determined based on the scattered signals of the scattered sampling points and of the interpolated sampling points, thereby improving the accuracy of determining the scattering of the rays forming the projection image.

In the embodiments, the scattering distribution map represents the distribution map of the overall scattered signals in the projection image. After the scattering distribution map is obtained, the projection image may be corrected based on the scattering distribution map to obtain a ray distribution map corresponding to the projection image.

Correcting the projection image based on the scattering distribution map includes calculating a difference value between the projection image and the scattering distribution map. By subtracting corresponding scattered signals from the second image, the scattering correction of the second image can be realized, and the distribution map of rays passing through the object to be detected can be obtained.

Optionally, in the embodiments, the step of correcting the second image based on the scattering distribution map to obtain the ray distribution map includes:

(1) determining a ray signal of a target projection area that is not occluded by the barrier posts in the projection image;
(2) determining a scattered signal of a target scattering area corresponding to the target projection area in the scattering distribution map; and
(3) correcting the ray signal of the target projection area based on the scattered signal of the target scattering area to obtain the ray distribution map.

Signals of areas that are occluded in the projection image are scattered signals, and correspondingly, signals of areas that are not occluded in the projection image are ray signals of the imaging source. Therefore, performing scattering correction on the signals of the areas in the projection image that are not occluded based on the scattering distribution map may include first determining a target projection area that is not occluded by the barrier posts in the projection image and a ray signal of the target projection area, determining a target scattering area corresponding to the target projection area in the scattering distribution map and a scattered signal of the target scattering area, and correcting the ray signal of the target projection area based on the scattered signal of the target scattering area to obtain a ray distribution map.

Determining the target scattering area corresponding to the target projection area in the scattering distribution map and the scattered signal of the target scattering area may include finding an area with the same position in the scattering distribution map based on the position of the target projection area. Afterwards, the found area is taken as the target scattering area, and then the scattered signal of the target scattering area is obtained.

In the embodiments, the positions of the target scattering area and the target projection area are the same, the signal of the target scattering area is a scattered signal, and the signal of the target projection area includes a main ray signal passing through the object to be detected and a scattered signal. Therefore, to correct the ray signal in the target projection area, it is necessary to remove the scattered signal therein. At the same time, due to the occlusion of the barrier posts, the area in the projection image that is occluded will lack the main ray signal. Therefore, it is still necessary to complement the main ray signal for the area that is occluded.

Based on this, in the embodiments, the step of correcting the ray signal of the target projection area based on the scattered signal of the target scattering area to obtain the ray distribution may include:

calculating a difference value between the ray signal of the target projection area and the scattered signal of the target scattering area to obtain an initial distribution map;
determining ray points to be interpolated in the initial distribution map based on the positions of the scattered sampling points; and
interpolating the ray points to be interpolated based on the ray signal in the initial distribution map to obtain a ray distribution map.

Calculating the difference value between the ray signal of the target projection area and the scattered signal of the target scattering area may include subtracting the value of the ray signal of the target projection area from the value of the scattered signal of the target scattering area to obtain the value of the main ray signal of the target projection area, so as to obtain the initial distribution map.

For an area that is not occluded by the barrier posts, the value of its main ray signal needs to be greater than 0. Therefore, to calculate the difference value between the ray signal of the target projection area and the scattered signal of the target scattering area, it is necessary to truncate the value of the scattered signal of the target scattering area based on the value of the ray signal of the target projection area, such that the value of the scattered signal of the target scattering area is smaller than the value of the ray signal of the target projection area.

Truncating the value of the scattered signal of the target scattering area based on the value of the ray signal of the target projection area may include detecting whether the value of the scattered signal of the target scattering area is greater than or equal to the value of the ray signal of the target projection area. If the value of the scattered signal of the target scattering area is greater than or equal to the value of the ray signal in the target projection area, it is necessary to recalculate the value of the scattered signal in the target scattering area such that the value of the scattered signal in the target scattering area is smaller than the value of the ray signal in the target projection area.

In an optional embodiment, the value of the scattered signal of the target scattering area may be recalculated based on scattered signals of adjacent areas around the target scattering area. By way of example, a parameter index such as an average value or variance of the scattered signals in the surrounding adjacent areas is calculated, and the parameter index is taken as the value of the scattered signal in target scattering area. A mapping relationship between a signal interval and a value signal may be established based on multiple test data. Recalculating the scattered signal of the target scattering area includes looking up for a target signal interval where the scattered signal of the target area is located, then looking up for a target value signal corresponding to the target signal interval based on the mapping relationship, and taking the value of the target value signal as the value of the scattered signal in the target scattering area.

In the embodiments, by calculating the difference value between the ray signal of the target projection area and the scattered signal of the target scattering area, the scattered signal in the ray signal of the target projection area can be removed, and the scattering correction of the projection area can be realized.

Due to the occlusion of the barrier posts, an area that is occluded will lack the main ray signal. Therefore, after the initial distribution map is obtained, it is necessary to complement the main ray signal in the area that is occluded by the barrier post in the initial distribution map.

In the embodiments, since the position occluded by a barrier post is the position of a scattered sampling point, a ray point to be interpolated in the initial distribution map may be determined based on the position of the scattered sampling point. By way of example, for each of the scattered sampling points, a point at the same position is looked up in the initial distribution map based on the position of the scattered sampling point, and the found point is taken as a ray point to be interpolated. In this embodiment, for each of the scattered sampling points, a corresponding ray point can be found in the initial distribution map.

After the ray points to be interpolated in the initial distribution map are obtained, the ray points to be interpolated may be interpolated based on ray signals in the initial ray distribution to obtain a ray distribution map.

In the embodiments, one-dimensional interpolation or two-dimensional interpolation may be adopted to interpolate the ray points to be interpolated based on the ray signals in the initial distribution map. When one-dimensional interpolation is adopted, for each ray point, a signal value to be interpolated corresponding to the ray point is calculated based on values of ray signals of two points (pixels) adjacent to the ray point in the first direction or the second direction. The signal value refers to the value of the signal. By way of example, if ray point A is to be interpolated in the second direction, a signal value corresponding to ray point A needs to be calculated based on values of ray signals of two points on the left and right of ray point A. When two-dimensional interpolation is adopted, for each ray point, a signal value to be interpolated corresponding to the ray point is calculated based on values of ray signals of adjacent points around the ray point (including adjacent points in the first direction and the second direction). By way of example, if ray point A is to be interpolated, the signal value corresponding to ray point A needs to be calculated based on values of ray signals of four points above, below, left, and right of ray point A (i.e., adjacent points of ray point A in the horizontal direction and the vertical direction), calculate.

After the ray points in the initial distribution map are interpolated, the main ray signal in the projection image is complemented, and the ray distribution map corresponding to the projection image is obtained.

Figure 13:
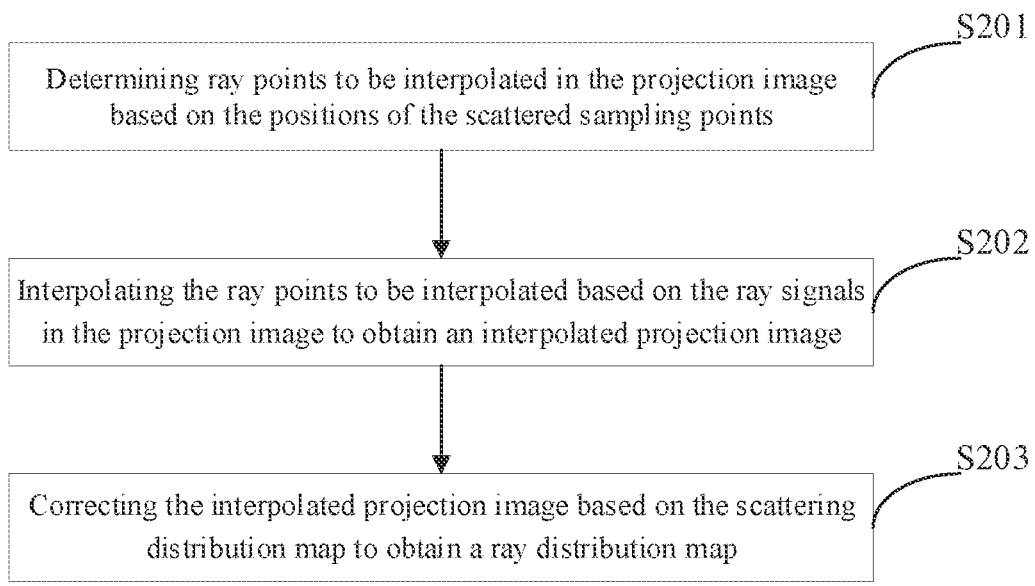
FIG. 13 is another schematic flowchart of the image acquisition method according to some embodiments of the present disclosure.

In an optional implementation, in this embodiment, a ray point to be interpolated in the projection image may be calculated first, and after the main ray signal of the ray point to be interpolated is completely complemented, scattering correction is performed. Based on this, FIG. 13 is another schematic flowchart of the image acquisition method according to some embodiments of the present disclosure. With reference to FIG. 13, in this embodiment, after the scattering distribution map corresponding to the projection image is obtained, the image acquisition method according to this embodiment further includes steps S201 to S203.

In step S201, ray points to be interpolated in the projection image are determined based on the positions of the scattered sampling points.

In step S202, the ray points to be interpolated are interpolated based on ray signals in the projection image to obtain an interpolated projection image.

In step S203, the interpolated projection image is corrected based on the scattering distribution map to obtain a ray distribution map.

Due to the occlusion of the barrier post, the scattered sampling point corresponding to the barrier post cannot receive the main ray signal. Therefore, it is necessary to interpolate and complement the main ray signal for the scattered sampling point. Based on this, in this embodiment, determining the ray points to be interpolated in the projection image based on the positions of the scattered sampling points may include taking each of the scattered sampling points in the projection image as a ray point to be interpolated in the projection image.

After the ray points to be interpolated in the projection image are determined, the ray points to be interpolated may be interpolated based on the ray signals in the projection image.

One-dimensional interpolation or two-dimensional interpolation may be adopted to interpolate the ray points to be interpolated based on the ray signals in the projection image. When one-dimensional interpolation is adopted, for each ray point, in the first direction or the second direction, a value of a signal to be interpolated corresponding to the ray point is calculated based on values of ray signals of two points (pixels) adjacent to the ray point. When two-dimensional interpolation is adopted, for each ray point, a value of a signal to be interpolated corresponding to the ray point is calculated based on values of ray signals of adjacent points around the ray point (including adjacent points in the first direction and the second direction).

After the ray points to be interpolated in the projection image are interpolated to obtain the interpolated projection image, the ray distribution in the projection image is obtained, but scattered signals still exist in the projection image in this case and shall be removed. Therefore, it is still necessary to correct the interpolated projection image based on the scattering distribution map to obtain a ray distribution map corresponding to the projection image.

Correcting the interpolated projection image based on the scattering distribution map may include directly calculating a difference value between the interpolated projection image and the scattering distribution map and removing the scattered signals in the interpolated projection image to realize scattering correction of the interpolated projection image.

In this embodiment, the ray distribution map represents a signal distribution map formed by the ray signals passing through the object to be detected. Based on the ray distribution map, image reconstruction may be performed. Therefore, after the projection image is corrected to obtain the ray distribution map, the image acquisition method according to this embodiment further includes:

calculating an attenuation integral image based on the ray distribution map and the projection image, and performing image reconstruction based on the attenuation integral image.

In order to accurately obtain the attenuation of the imaging beam when the object to be detected is being scanned, in this embodiment, the attenuation integral image may be calculated using the first image and the ray distribution image. The first image is a projection image formed when no object to be detected is placed, and the ray distribution map represents a signal distribution map formed by the ray signals passing through the object to be detected. Therefore, by parsing the values of the signals in the first image and the ray distribution map, the attenuation of the ray signals generated by the imaging source passing through the object to be detected can be accurately obtained.

Optionally, in this embodiment, the attenuation integral image may be obtained according to a formula $$L1 = -\ln\left(\frac{P2}{I1}\right)$$

based on the ray distribution map and the first image, where L1 is the attenuation integral image, P2 is the ray distribution map, and I1 is the first image. After the attenuation integral image is obtained, the attenuation integral image may be used for image reconstruction.

In this embodiment, algorithms such as analytical reconstruction or iterative reconstruction may be adopted for image reconstruction with the attenuation integral image, which may be set according to actual needs, and are not limited in this embodiment.

Figure 14:
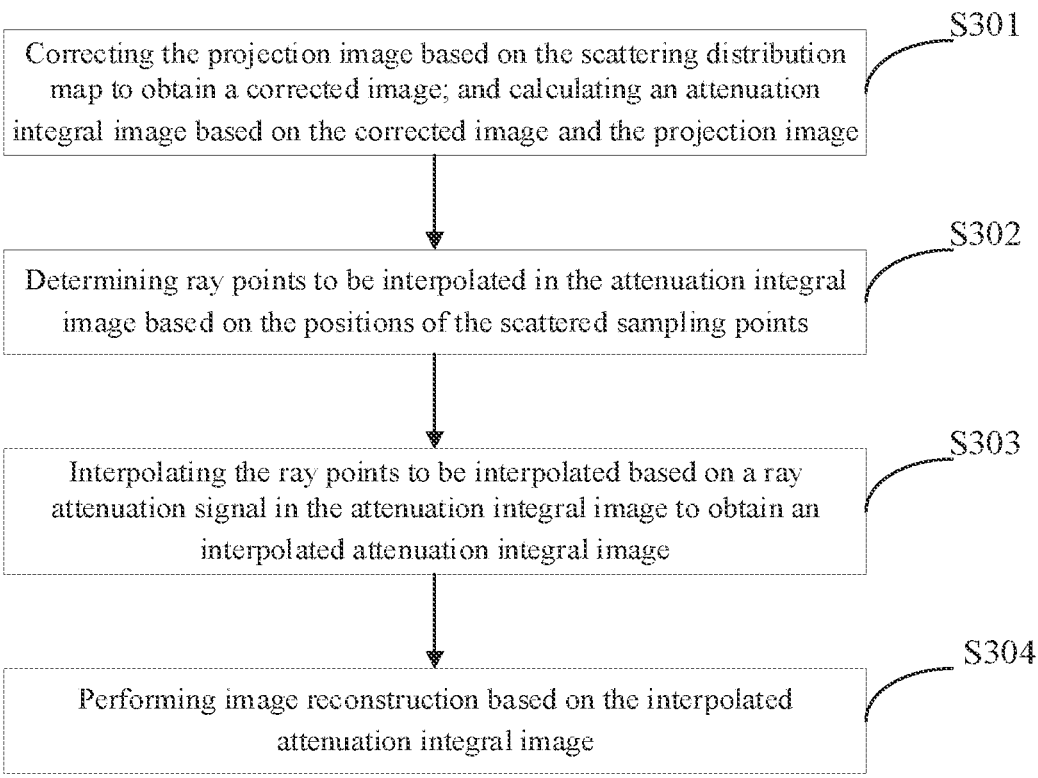
FIG. 14 is still another schematic flowchart of the image acquisition method according to some embodiments of the present disclosure.

In order to simplify steps and improve processing efficiency, in this embodiment, the attenuation integral image may be calculated first, and then the main ray signal of the occluded shaded area is complemented by the attenuation integral image. Based on this, FIG. 14 is another schematic flowchart of the image acquisition method according to some embodiments of the present disclosure. With reference to FIG. 14, after the scattering distribution map corresponding to the projection image is obtained, the method according to this embodiment may further include steps S301 to S304.

In step S301, the projection image is corrected based on the scattering distribution map to obtain a corrected image; and an attenuation integral image is calculated based on the corrected image and the projection image.

In step S302, ray points to be interpolated in the attenuation integral image are determined based on the positions of the scattered sampling points.

In step S303, the ray points to be interpolated are interpolated based on a ray attenuation signal in the attenuation integral image to obtain an interpolated attenuation integral image.

In step S304, image reconstruction is performed based on the interpolated attenuation integral image.

Correcting the projection image based on the scattering distribution map may include first determining a ray signal of a target projection area in the projection image that is not occluded by the barrier posts, and then determining a scattered signal of a target scattering area corresponding to the target projection area in the scattering distribution map, and finally calculating a difference value between the ray signal of the target projection area and the scattered signal of the target scattering area, and removing the scattered signal in the projection image to obtain a corrected image.

After the corrected image is obtained, the attenuation integral image may be calculated based on the corrected image and the projection image. In order to accurately obtain the attenuation of the imaging beam when the object to be detected is being scanned, in this embodiment, the attenuation integral image is calculated based on the first image and the corrected image. The attenuation integral image may be obtained according to a formula $$L2 = -\ln\left(\frac{P1}{I1}\right)$$

based on the corrected image and the first image, where L2 is the attenuation integral image, P1 is the corrected image, and I1 is the first image.

In this embodiment, the first image is a projection image formed when no object to be detected is placed, and the corrected image represents the signal distribution of the ray signals passing through the object to be detected. The attenuation integral image calculated based on the first image and the correction image represents the attenuation of the ray signals generated by the imaging source passing through the object to be detected, that is, a signal in the attenuation integral image is a signal after the ray signal is attenuated (i.e., a ray attenuation signal). Scattered sampling points that are consistent with the positions in the projection image exist in the attenuation integral image. Determining the ray points to be interpolated in the attenuation integral image based on the positions of the scattered sampling points may include first acquiring scattered sampling points in the attenuation integral image and then taking each of the scattered sampling points in the attenuation integral image as a ray point to be interpolated in the attenuation integral image.

After the ray points to be interpolated in the attenuation integral image are determined, the ray points to be interpolated may be interpolated based on ray attenuation signals in the attenuation integral image to obtain an interpolated attenuation integral image.

One-dimensional interpolation or two-dimensional interpolation may be adopted to interpolate the ray points to be interpolated based on the ray attenuation signals in the attenuation integral image. When one-dimensional interpolation is adopted, for each ray point, in the first direction or the second direction, a value of a signal to be interpolated corresponding to the ray point is calculated based on values of ray signals of two points (pixels) adjacent to the ray point. When two-dimensional interpolation is adopted, for each ray point, a value of a signal to be interpolated corresponding to the ray point is calculated based on values of ray signals of adjacent points around the ray point (including adjacent points in the first direction and the second direction).

After the interpolated attenuation integral image is obtained, the interpolated attenuation integral image may be used for image reconstruction.

In the image acquisition method according to this embodiment, by arranging staggered vacancies between the barrier posts, the shaded areas that are occluded in the projection image can be reduced. Furthermore, through the above process, when the main ray signal of the projection image is interpolated and complemented, the amount of interpolation can be reduced, the errors caused by interpolation during image reconstruction can be reduced, and the artifacts of the reconstructed image can be reduced.

In the image acquisition method according to this embodiment, an imaging beam is occluded by arranging a barrier array plate, a vacancy between every adjacent scattered sampling points is interpolated using the low-frequency smoothness characteristic of the scattered signal distribution, and then the distribution information of the scattered signals in the projection image can be accurately determined based on the scattered signals of the scattered sampling points and of the interpolated sampling points, improving the accuracy of determining the scattering of the rays forming the projection image. In addition, in this embodiment, the intersection of the central axes of the barrier posts is in coincidence with the imaging focal point of the imaging source, which ensures that the ranges of the shaded areas are consistent, and further improves the accuracy of determining the scattering.

On the basis of the above, this embodiment further provides a readable storage medium having a computer program stored therein. When the computer program runs, it controls the calibration equipment where the readable storage medium is located to implement the image acquisition method described in any of the above embodiments.

The readable storage medium may be (but is not limited to) various media that can store program codes such as a U disk, a mobile hard disk, a read-only memory (ROM), a random access memory (RAM), a magnetic disk or an optical disk.

Those skilled in the art can clearly understand that for the convenience and brevity of the description, for the specific working process of the above readable storage medium, reference may be made to the corresponding process in the above method, which will not be repeated here.

In summary, in the image acquisition method, imaging system, calibration equipment and storage medium according to some embodiments of the present disclosure, an imaging beam is occluded by arranging a barrier array plate, a vacancy between every adjacent scattered sampling points is interpolated, and then the distribution of the scattered signals in the projection image can be effectively determined based on the scattered signals of the scattered sampling points and of the interpolated sampling points, improving the accuracy of determining the scattering of the rays forming the projection image. Furthermore, by reducing the number of barrier posts of the barrier array plate in the irradiation area of the imaging source, the number of shaded areas in the projection image acquired by the imager is reduced. In this way, errors caused by interpolation during image reconstruction based on the projection image can be reduced.

The image acquisition method, imaging system, correction equipment, and storage medium according to the embodiments of the present disclosure have been described in detail above. Herein, specific examples are given to illustrate the principles and implementation methods of the present disclosure. The description of the above embodiments is only intended to help understand the technical solutions and core ideas of the present disclosure. Those skilled in the art should understand that they can still modify the technical solutions recorded in the above embodiments, or perform equivalent replacements for some of the technical features, and these modifications or replacements do not make the essence of the corresponding technical solutions depart from the scope of the technical solutions of the various embodiments of the present disclosure.

What is claimed is:

1. An image acquisition method, comprising:
acquiring a projection image formed by an imaging beam passing through a barrier array plate, wherein the barrier array plate comprises a plurality of barrier posts;
acquiring scattered sampling points corresponding to the barrier posts in the projection image, wherein the scattered sampling points are disposed in shaded areas that are occluded by the barrier posts in the projection image;
interpolating a vacancy between every adjacent scattered sampling points based on scattered signals of the scattered sampling points to obtain interpolated sampling points, a scattered signal of any point in the projection image referring to a scattered ray signal in a ray signal forming the point, and the vacancy referring to an area between shaded areas where every adjacent scattered sampling points are located; and
acquiring a scattering distribution map corresponding to the projection image based on the scattered signals of the scattered sampling points and of the interpolated sampling points, wherein the scattering distribution map is configured to characterize scattering of the imaging beam.

2. The method according to claim 1, wherein the projection image comprises a first image formed in a case that no object to be detected is placed and a second image formed in a case that an object to be detected is placed; and
said acquiring the scattered sampling points corresponding to the barrier posts in the projection image comprises:
acquiring center points of shaded areas that are occluded by the barrier posts in the first image; and
acquiring target points corresponding to the center points of the shaded areas in the second image based on the center points of the shaded areas, and determining the target points as the scattered sampling points in the second image.

3. The method according to claim 1, wherein said interpolating the vacancy between every adjacent scattered sampling points based on the scattered signals of the scattered sampling points to obtain the interpolated sampling points comprises:
acquiring scattered signals of set pixel ranges where the scattered sampling points are located; and
interpolating the vacancy between every adjacent scattered sampling points based on the scattered signals of the set pixel ranges where the scattered sampling points are located to obtain the interpolated sampling points.

4. The method according to claim 3, wherein said acquiring the scattering distribution map corresponding to the projection image based on the scattered signals of the scattered sampling points and of the interpolated sampling points comprises:
acquiring the scattering distribution map by performing interpolation or fitting between the scattered sampling points and the interpolated sampling points based on the scattered signals of the set pixel ranges where the scattered sampling points are located and the scattered signals of the interpolated sampling points.

5. The method according to claim 1, wherein said interpolating the vacancy between every adjacent scattered sampling points based on the scattered signals of the scattered sampling points to obtain the interpolated sampling points comprises:
   interpolating the vacancy between every adjacent scattered sampling points respectively in a first direction and a second direction perpendicular to each other to obtain two auxiliary sampling points corresponding to the first direction and the second direction respectively;
   acquiring the interpolated sampling point based on the two auxiliary sampling points.

6. The method according to claim 5, wherein said acquiring the interpolated sampling points based on the two auxiliary sampling points comprises:
   determining an auxiliary sampling point corresponding to a target direction in the first direction and the second direction as the interpolated sampling point;
   wherein for any vacancy in the projection image, the target direction satisfies at least one of:
   adjacent scattered sampling points being disposed on two sides of the vacancy only in the target direction in the first direction and the second direction; or
   adjacent scattered sampling points being disposed on two sides of the vacancy both in the first direction and in the second direction, wherein the target direction is the second direction in a case that the second direction satisfies a target condition, or the target direction is the first direction in a case that the second direction does not satisfy the target condition, the target condition comprises at least one of: in the first direction and the second direction, an absolute value of a difference value between the scattered signals of the two scattered sampling points on two sides of the vacancy in the second direction being minimum, or a value of the scattered signal of the auxiliary sampling point corresponding to the second direction being minimum.

7. The method according to claim 1, wherein said acquiring the scattered sampling points corresponding to the barrier posts in the projection image, the method further comprises:
   obtaining ray signals of the scattered sampling points;
   determining equivalent water thicknesses of the scattered sampling points based on the ray signals of points around the shaded areas where the scattered sampling points are located in the first image and the second image, where an attenuation of the ray signal of the scattered sampling point is the same as an attenuation of the ray signal in the imaging beam in water of the equivalent water thickness; and
   acquiring the scattered signals of the scattered sampling points by correcting the ray signals of the scattered sampling points based on a correction ratio corresponding to the equivalent water thicknesses of the scattered sampling points, wherein the correction ratio is positively correlated to the equivalent water thickness.

8. The method according to claim 1, wherein after acquiring the scattering distribution map corresponding to the projection image, the method further comprises one of:
   acquiring a ray distribution map by correcting the projection image based on the scattering distribution map; or
   determining ray points to be interpolated in the projection image based on the positions of the scattered sampling points; interpolating the ray points to be interpolated based on the ray signals in the projection image to obtain an interpolated projection image; and acquiring a ray distribution map by correcting the interpolated projection image based on the scattering distribution map.

9. The method according to claim 8, wherein said acquiring the ray distribution map by correcting the interpolated projection image based on the scattering distribution map comprises:
   determining ray signals of a target projection area in the projection image that is not occluded by the barrier posts;
   determining scattered signals of a target scattering area corresponding to the target projection area in the scattering distribution map; and
   acquiring the ray distribution map by correcting the ray signals of the target projection area based on the scattered signals of the target scattering area.

10. The method according to claim 9, wherein said acquiring the ray distribution map by correcting the ray signals of the target projection area based on the scattered signals of the target scattering area comprises:
    acquiring an initial distribution map by performing difference calculation on the ray signals of the target projection area and the scattered signals of the target scattering area;
    determining ray points to be interpolated in the initial distribution map based on the positions of the scattered sampling points; and
    acquiring the ray distribution map by interpolating the ray points to be interpolated based on the ray signals in the initial distribution map.

11. The method according to claim 8, wherein after said acquiring the ray distribution map, the method further comprises:
    calculating an attenuation integral image based on the ray distribution map and the projection image, and performing image reconstruction based on the attenuation integral image.

12. The method according to claim 1, wherein after acquiring the scattering distribution map corresponding to the projection image, the method further comprises:
    acquiring a corrected image by correcting the projection image based on the scattering distribution map, and calculating an attenuation integral image based on the corrected image and the projection image;
    determining ray points to be interpolated in the attenuation integral image based on the positions of the scattered sampling points;
    acquiring an interpolated attenuation integral image by interpolating the ray points to be interpolated based on ray attenuation signals in the attenuation integral image; and
    performing image reconstruction based on the interpolated attenuation integral image.

13. An imaging system comprising:
    a gantry;
    an imaging source disposed on the gantry;
    an imager disposed on the gantry opposite to the imaging source;
    a barrier array plate gantry between the imaging source and the imager, wherein the barrier array plate comprises a plurality of barrier posts;
    calibration equipment connected to the imager, wherein the calibration equipment is configured to:
    acquire a projection image formed by an imaging beam passing through the barrier array plate; acquire scattered sampling points corresponding to the barrier posts in the projection image, wherein the scattered sampling points are disposed in shaded areas that are occluded by the barrier posts in the projection image; interpolate a vacancy between every adjacent scattered sampling points based on scattered signals of the scattered sampling points to obtain interpolated sampling points, a scattered signal of any point in the projection image referring to a scattered ray signal in a ray signal forming the point, and the vacancy referring to an area between shaded areas where every adjacent scattered sampling points are located; and acquire a scattering distribution map corresponding to the projection image based on the scattered signals of the scattered sampling points and of the interpolated sampling points, wherein the scattering distribution map is configured to characterize scattering of the imaging beam.

14. The imaging system according to claim 13, wherein the barrier array plate is provided with a plurality of rows of posts in a first direction, and each row of posts comprises a plurality of barrier posts arranged in a second direction, and wherein the barrier posts in adjacent rows of posts are staggered from each other, and the first direction is perpendicular to the second direction.

15. The imaging system according to claim 14, wherein an intersection of central axes of the barrier posts is in coincidence with an imaging focal point of the imaging source.

16. The imaging system according to claim 13, further comprising:
an array plate drive device disposed on the gantry and connected to the barrier array plate and the calibration equipment respectively,
wherein the array plate drive device is configured to drive the barrier array plate to rotate under the control of the calibration equipment.

17. Calibration equipment comprising a processor and a memory storing a computer program executable by the processor, wherein the processor, when loading and executing the computer program, is caused to perform:
acquiring a projection image formed by an imaging beam passing through a barrier array plate, wherein the barrier array plate comprises a plurality of barrier posts;
acquiring scattered sampling points corresponding to the barrier posts in the projection image, wherein the scattered sampling points are disposed in shaded areas that are occluded by the barrier posts in the projection image;
interpolating a vacancy between every adjacent scattered sampling points based on scattered signals of the scattered sampling points to obtain interpolated sampling points, a scattered signal of any point in the projection image referring to a scattered ray signal in a ray signal forming the point, and the vacancy referring to an area between shaded areas where every adjacent scattered sampling points are located; and
acquiring a scattering distribution map corresponding to the projection image based on the scattered signals of the scattered sampling points and of the interpolated sampling points, wherein the scattering distribution map is configured to characterize scattering of the imaging beam.

18. A non-transitory storage medium storing a computer program therein, wherein the computer program, when loaded and executed by a processor, causes the processor to perform the method as defined in claim 1.

19. A computer program product comprising instructions, wherein the computer program product when run by a computer, causes the computer to perform the method as defined in claim 1.

20. A chip comprising at least one of programmable logic circuits and program instructions, wherein the chip, when running, implements the method as defined in claim 1.

* * * * *